United States Patent
Bates et al.

(10) Patent No.: US 8,080,034 B2
(45) Date of Patent: Dec. 20, 2011

(54) VASCULAR HEMOSTASIS DEVICE AND DEPLOYMENT APPARATUS

(75) Inventors: James S. Bates, Sparta, NJ (US); Peter Hinchliffe, Campbell Hall, NY (US)

(73) Assignee: St. Jude Medical, Inc., St. Paul, MN (US)

( * ) Notice: Subject to any disclaimer, the term of this patent is extended or adjusted under 35 U.S.C. 154(b) by 697 days.

(21) Appl. No.: 12/009,830

(22) Filed: Jan. 22, 2008

(65) Prior Publication Data
US 2008/0243182 A1    Oct. 2, 2008

Related U.S. Application Data

(60) Provisional application No. 60/920,640, filed on Mar. 29, 2007.

(51) Int. Cl.
*A61B 17/08* (2006.01)
*A61D 1/00* (2006.01)

(52) U.S. Cl. ...................................... 606/213

(58) Field of Classification Search .................. 606/213, 606/215–218, 151; 411/340–345
See application file for complete search history.

(56) References Cited

U.S. PATENT DOCUMENTS

| | | | | |
|---|---|---|---|---|
| 2,638,774 A * | 5/1953 | Wieman | ........................ | 52/514 |
| 4,286,497 A * | 9/1981 | Shamah | ........................ | 411/342 |
| 4,796,612 A * | 1/1989 | Reese | ........................ | 606/324 |
| 4,865,501 A * | 9/1989 | Ferris | ........................ | 411/340 |
| 5,226,767 A * | 7/1993 | Foerster, Jr. | ........................ | 411/340 |
| 5,282,827 A | 2/1994 | Kensey et al. | | |
| 5,342,393 A * | 8/1994 | Stack | ........................ | 606/213 |
| 5,350,399 A * | 9/1994 | Erlebacher et al. | ........... | 606/213 |
| 5,370,646 A * | 12/1994 | Reese et al. | ........................ | 606/324 |
| 5,370,661 A * | 12/1994 | Branch | ........................ | 606/232 |
| 5,437,631 A | 8/1995 | Janzen | | |
| 5,478,353 A * | 12/1995 | Yoon | ........................ | 606/213 |
| 5,593,422 A | 1/1997 | Van de Moer et al. | | |
| 5,620,461 A | 4/1997 | Van De Moer et al. | | |
| 5,676,689 A | 10/1997 | Kensey et al. | | |
| 5,875,606 A * | 3/1999 | Jensen | ........................ | 411/340 |
| 5,916,236 A | 6/1999 | Van de Moer et al. | | |
| 6,007,563 A | 12/1999 | Nash et al. | | |
| 6,022,351 A * | 2/2000 | Bremer et al. | ........................ | 606/324 |
| 6,074,401 A * | 6/2000 | Gardiner et al. | ........................ | 606/139 |
| 6,090,130 A | 7/2000 | Nash et al. | | |
| 6,485,493 B1 * | 11/2002 | Bremer | ........................ | 606/70 |
| 6,491,714 B1 * | 12/2002 | Bennett | ........................ | 606/232 |
| 6,596,013 B2 * | 7/2003 | Yang et al. | ........................ | 606/215 |
| 6,821,069 B2 * | 11/2004 | Ikuta | ........................ | 411/344 |
| 6,860,895 B1 * | 3/2005 | Akerfeldt et al. | ........... | 606/215 |
| 7,048,737 B2 * | 5/2006 | Wellisz et al. | ........... | 606/70 |
| 7,048,738 B1 * | 5/2006 | Wellisz et al. | ........... | 606/70 |

(Continued)

*Primary Examiner* — Corrine M McDermott
*Assistant Examiner* — Dianne Dornbusch
(74) *Attorney, Agent, or Firm* — Holland & Hart

(57) ABSTRACT

A hemostasis device for percutaneously sealing a puncture in the wall of a blood vessel includes a rigid post, and a foot, a seal and a retaining member mounted on the rigid post. The hemostasis device may be deployed in the puncture so that the foot is positioned within the blood vessel. Tension is applied to the rigid post to hold the foot against the inside surface of the blood vessel. The retaining member is then pushed along the length of the rigid post, advancing the seal to a deployed state against the outside surface of the blood vessel. The puncture in the blood vessel is sandwiched between the foot and the seal in the deployed state. The rigid post, foot, seal and retaining member may all be formed from a resorbable polymeric material.

48 Claims, 18 Drawing Sheets

U.S. PATENT DOCUMENTS

| | | | |
|---|---|---|---|
| 7,338,514 B2 * | 3/2008 | Wahr et al. | 606/213 |
| 7,632,287 B2 * | 12/2009 | Baker et al. | 606/151 |
| 2002/0177850 A1 * | 11/2002 | Bremer | 606/70 |
| 2002/0183787 A1 * | 12/2002 | Wahr et al. | 606/213 |
| 2003/0229349 A1 * | 12/2003 | Wellisz et al. | 606/72 |
| 2004/0044364 A1 * | 3/2004 | DeVries et al. | 606/213 |
| 2005/0085852 A1 * | 4/2005 | Ditter | 606/213 |
| 2005/0159777 A1 * | 7/2005 | Spitz | 606/213 |
| 2005/0228415 A1 * | 10/2005 | Gertner | 606/153 |
| 2005/0273135 A1 * | 12/2005 | Chanduszko et al. | 606/213 |
| 2008/0253860 A1 * | 10/2008 | McDuff et al. | 411/344 |

* cited by examiner

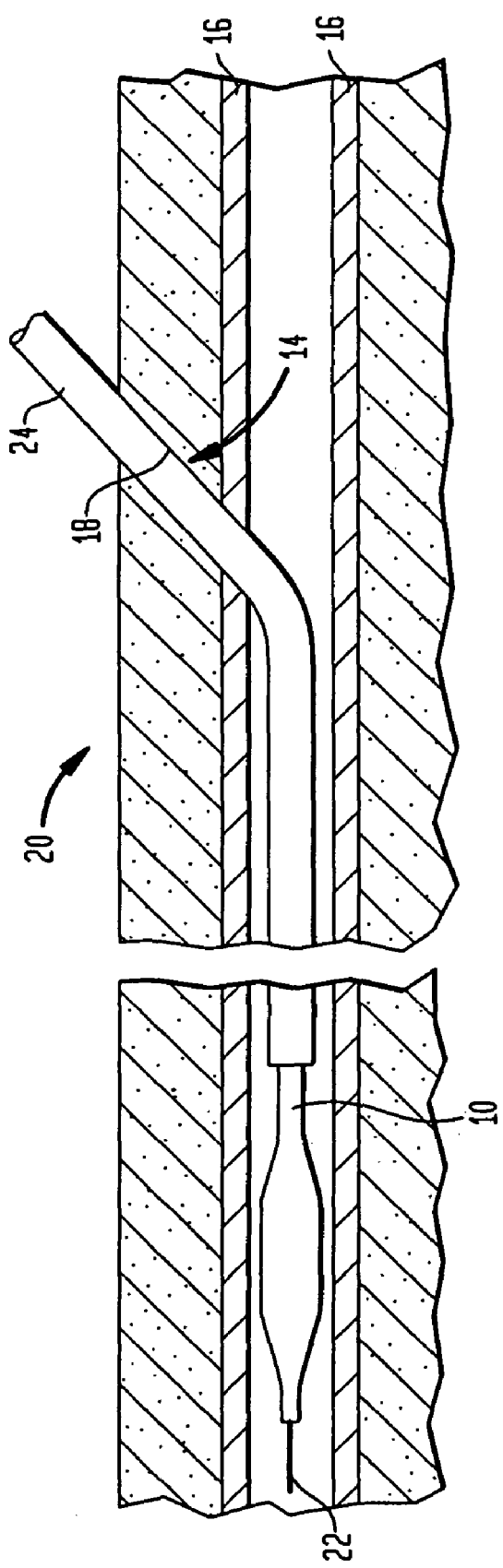

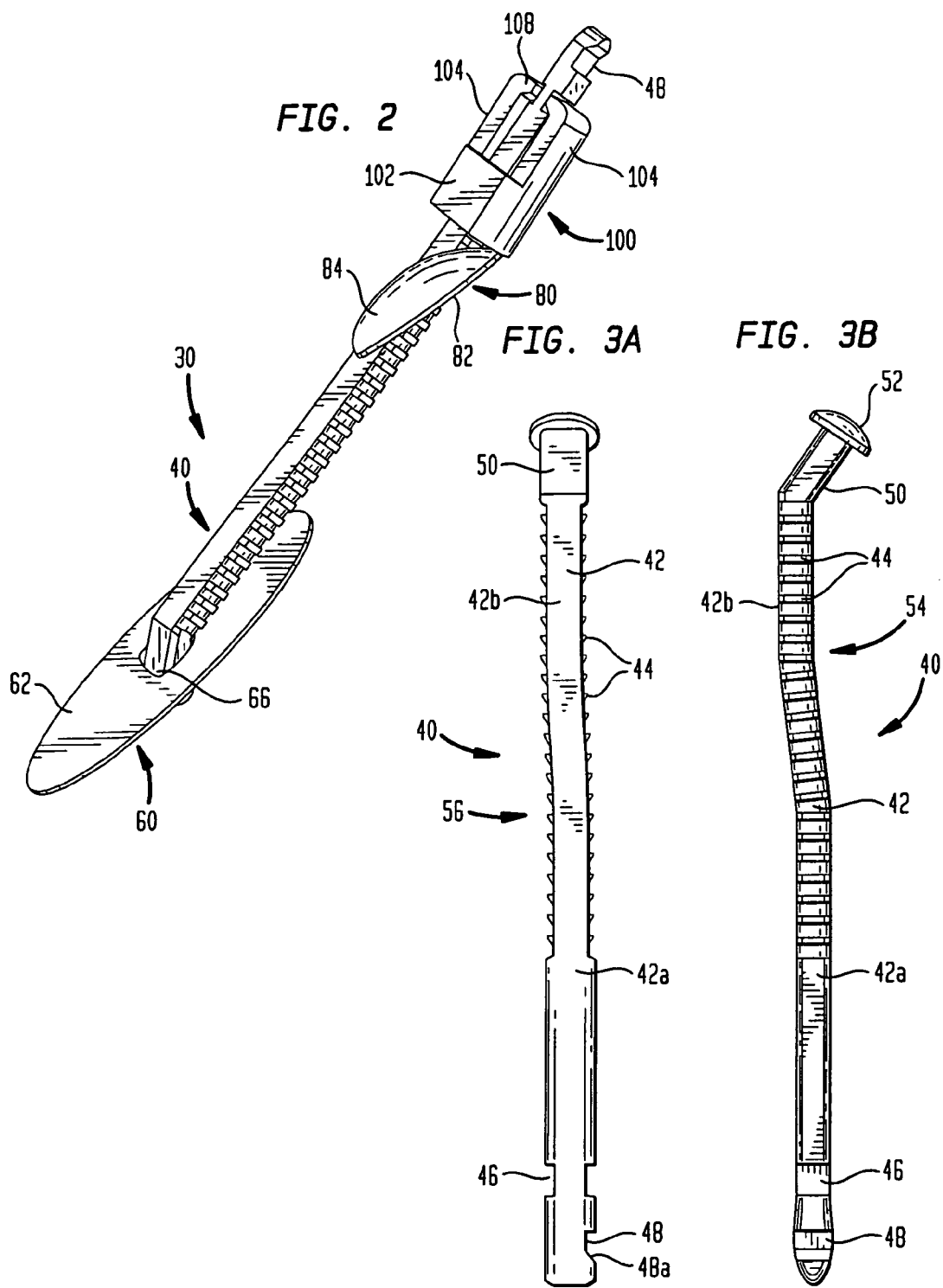

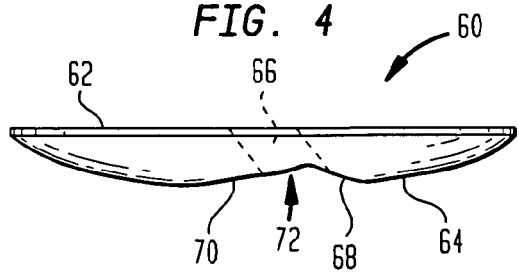
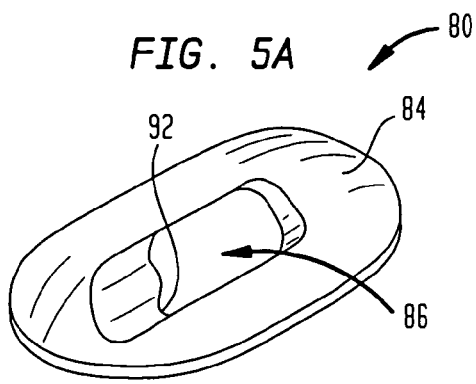
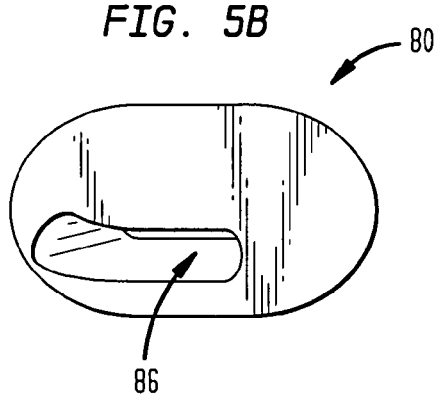
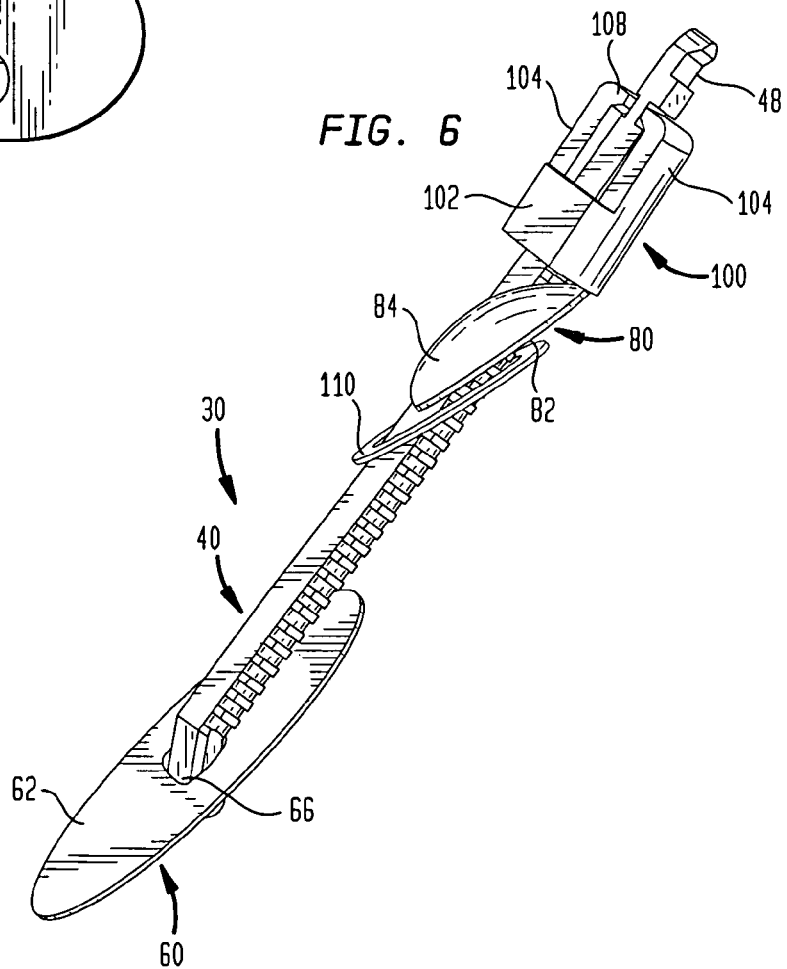

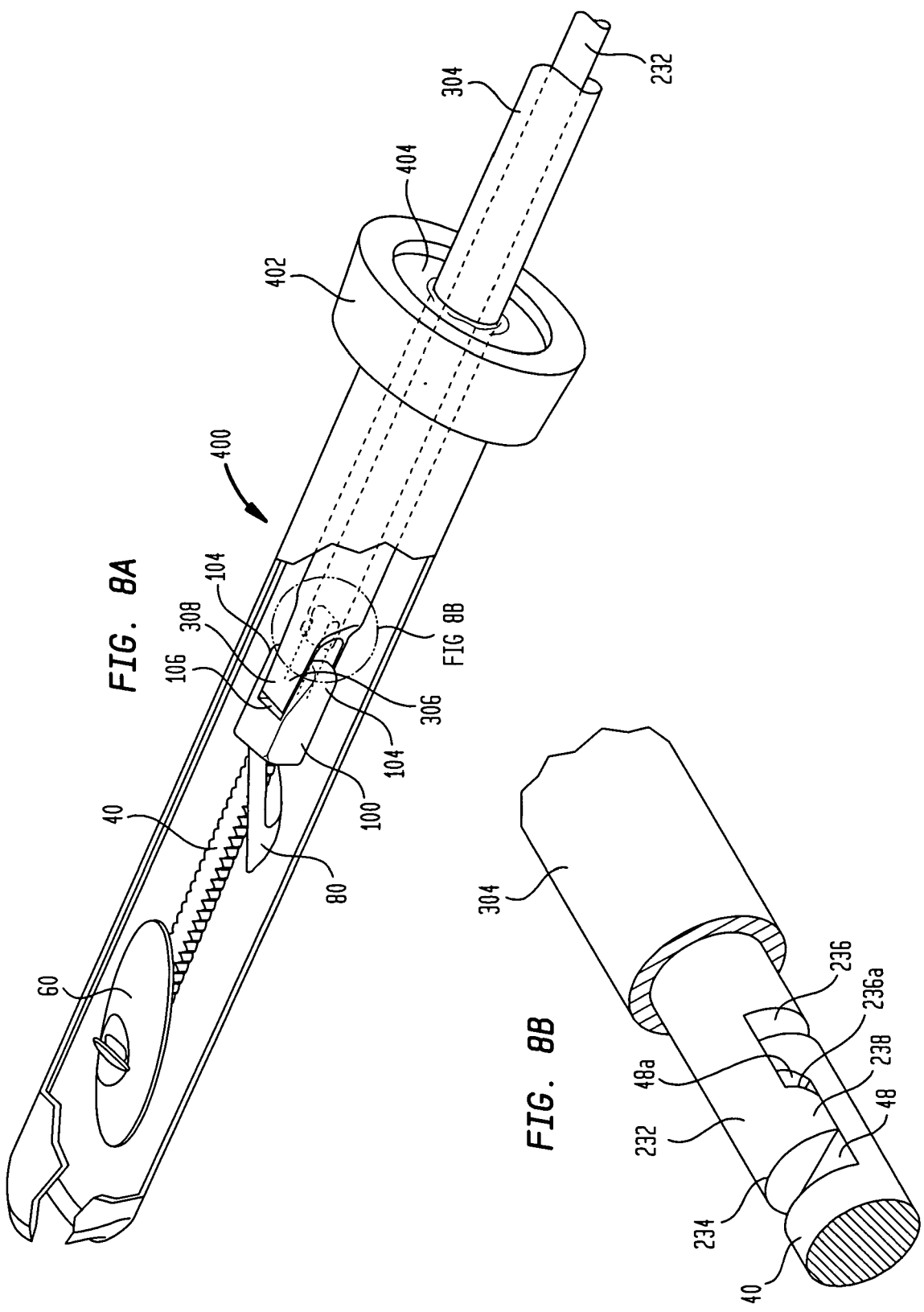

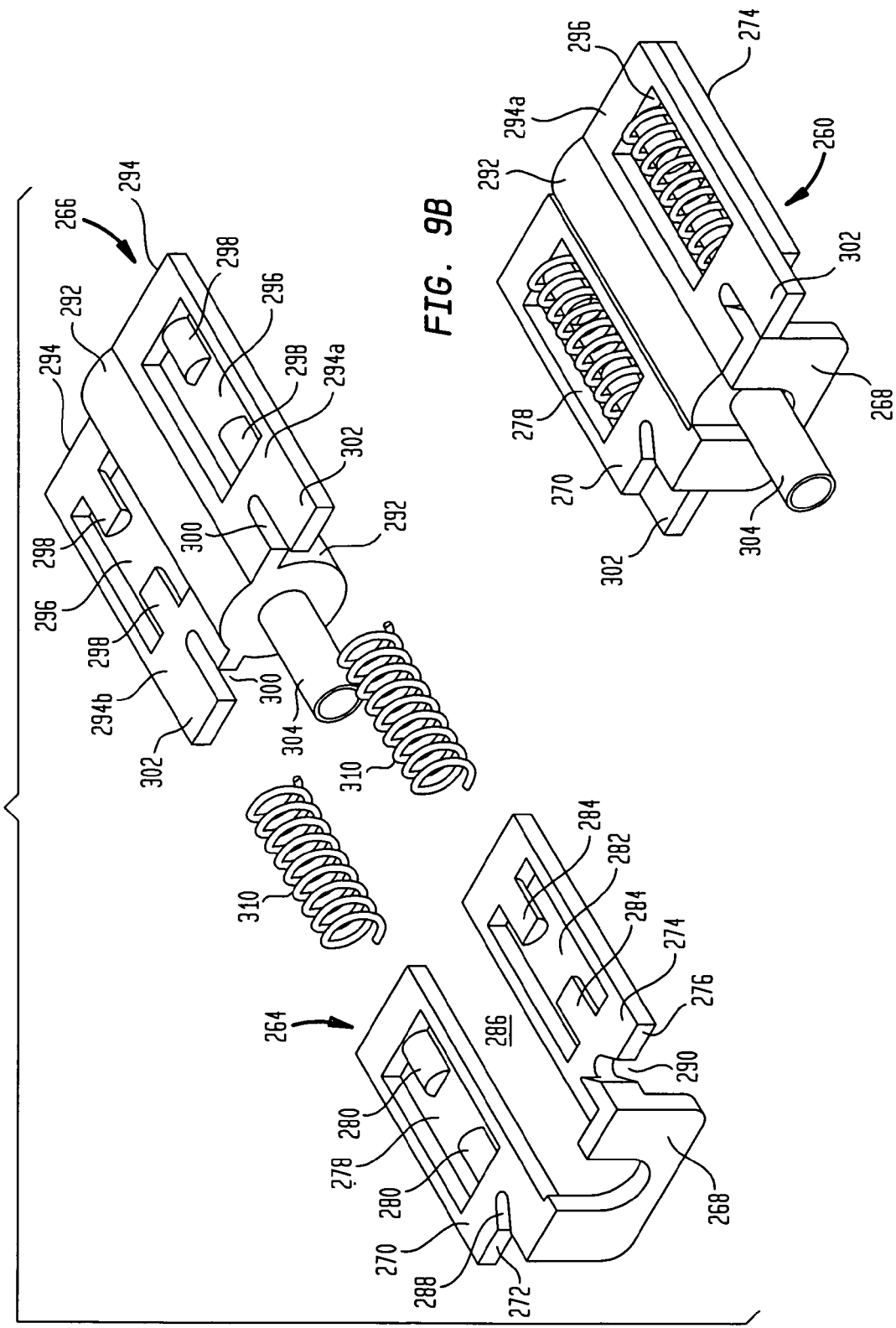

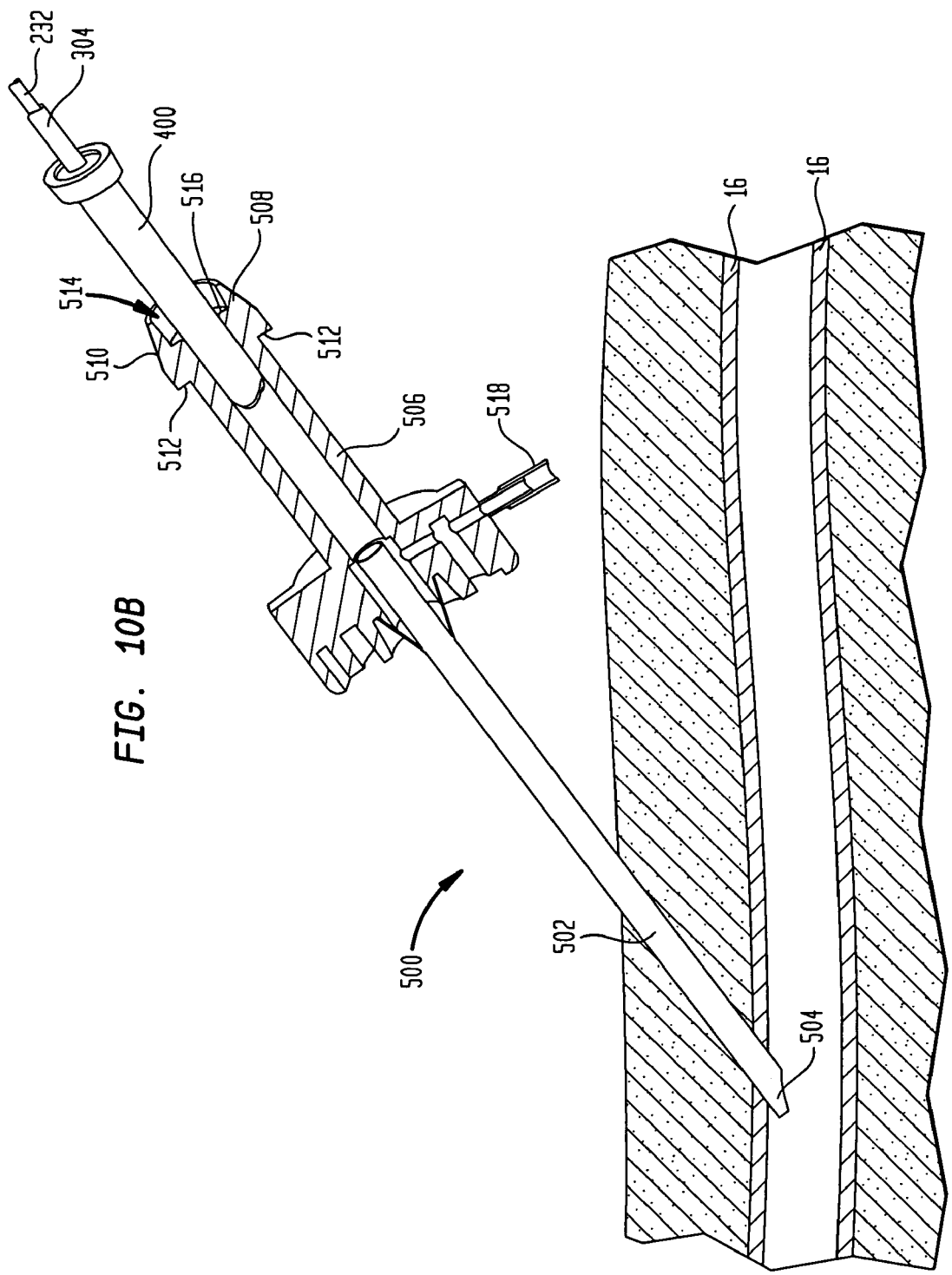

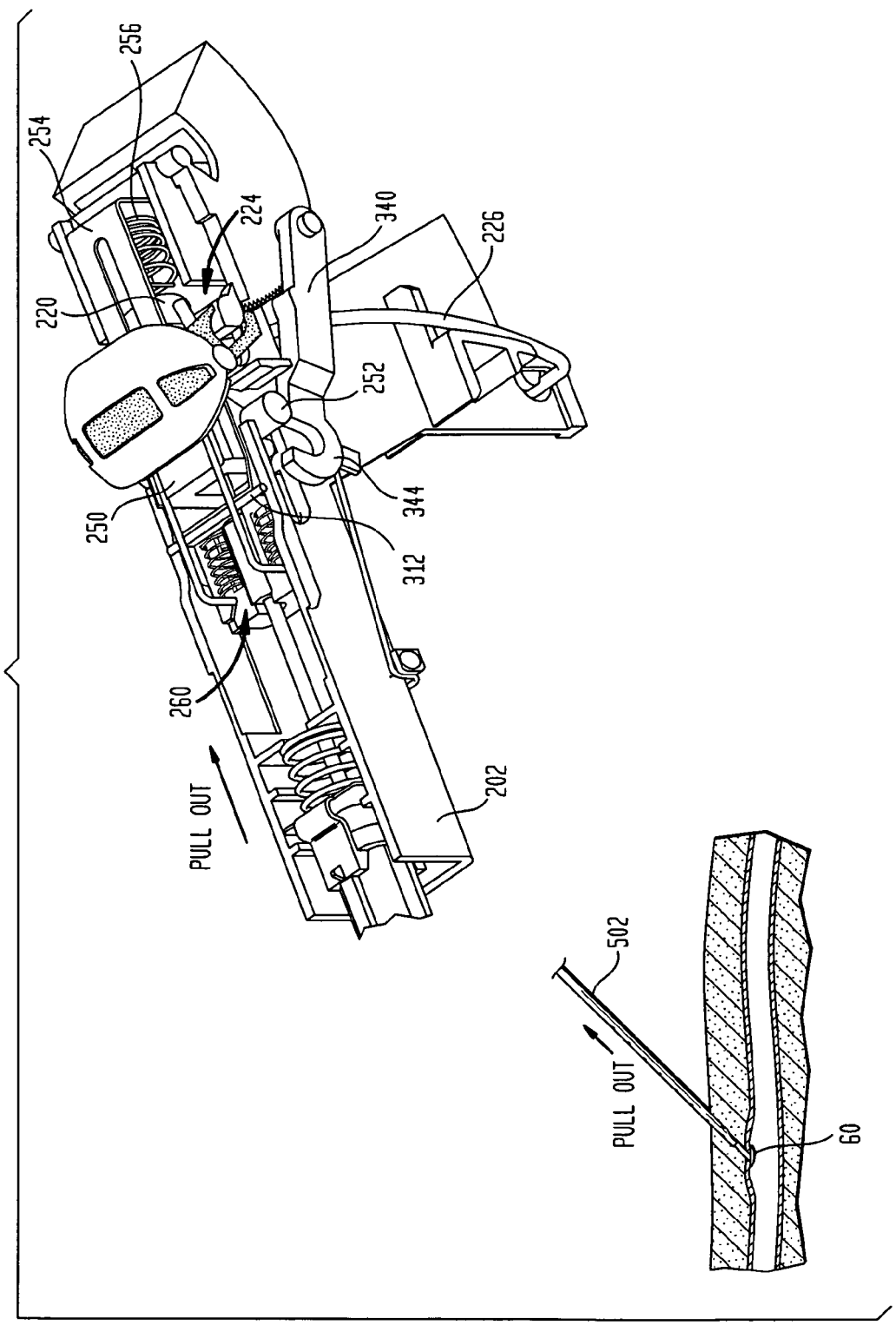

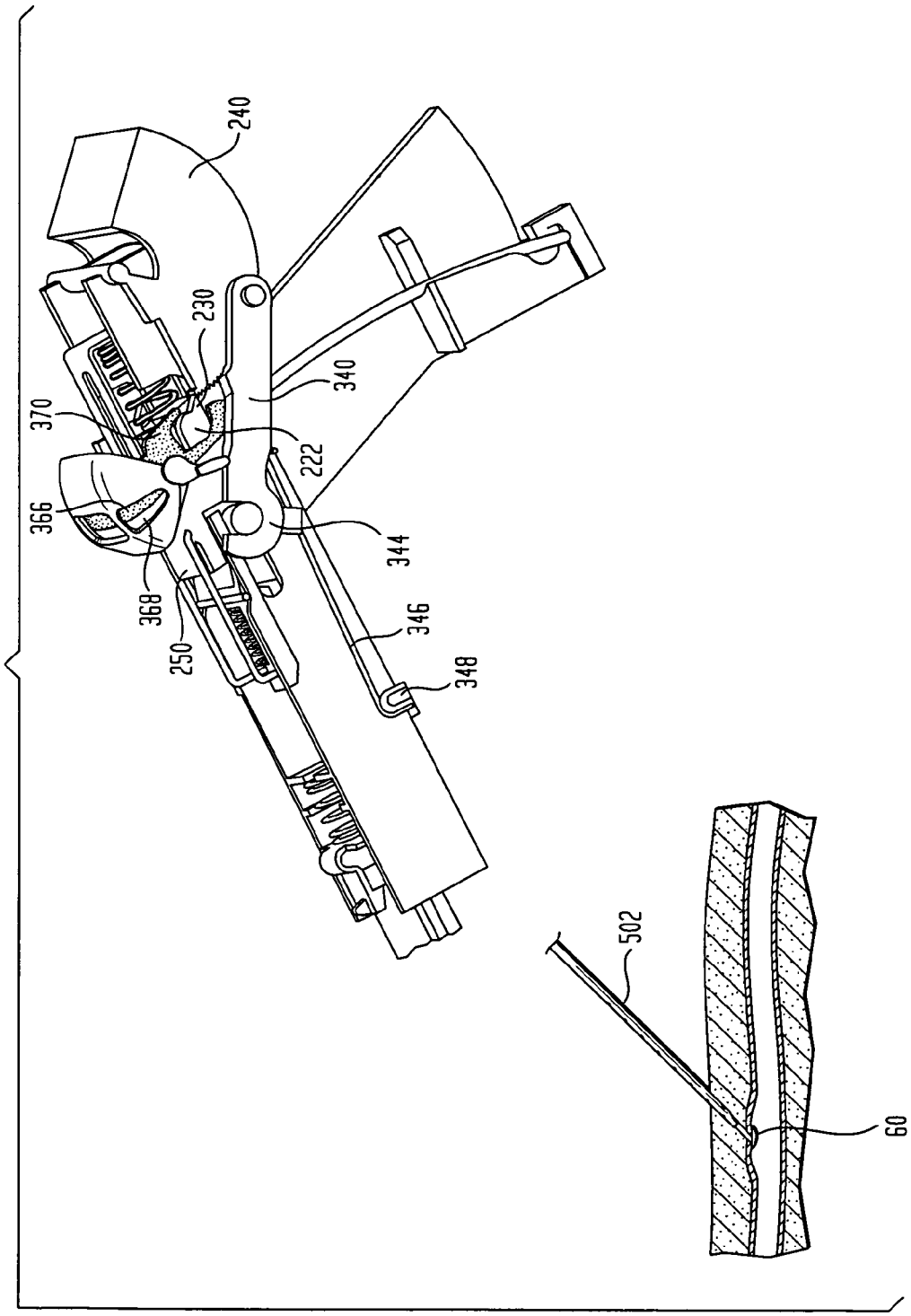

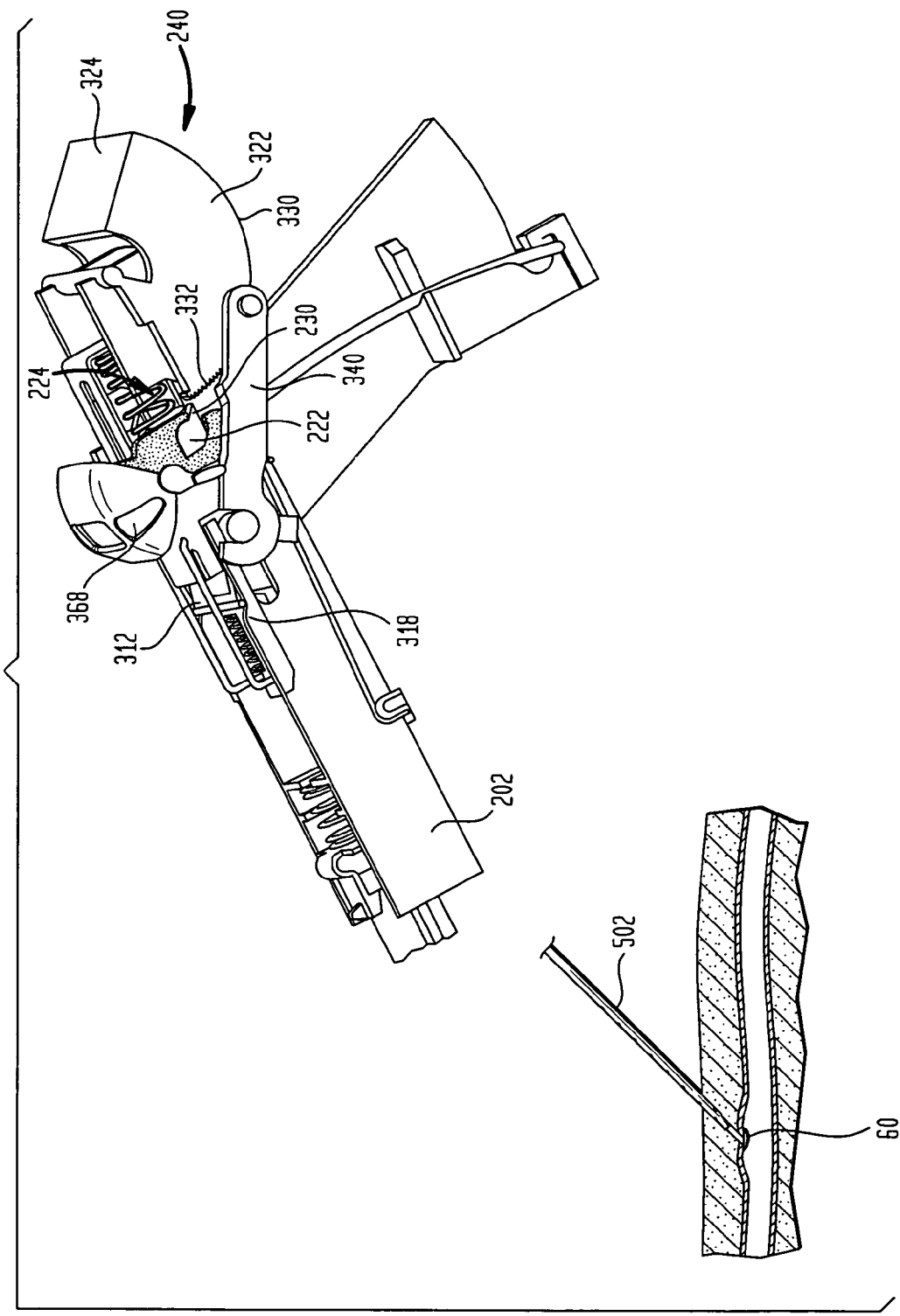

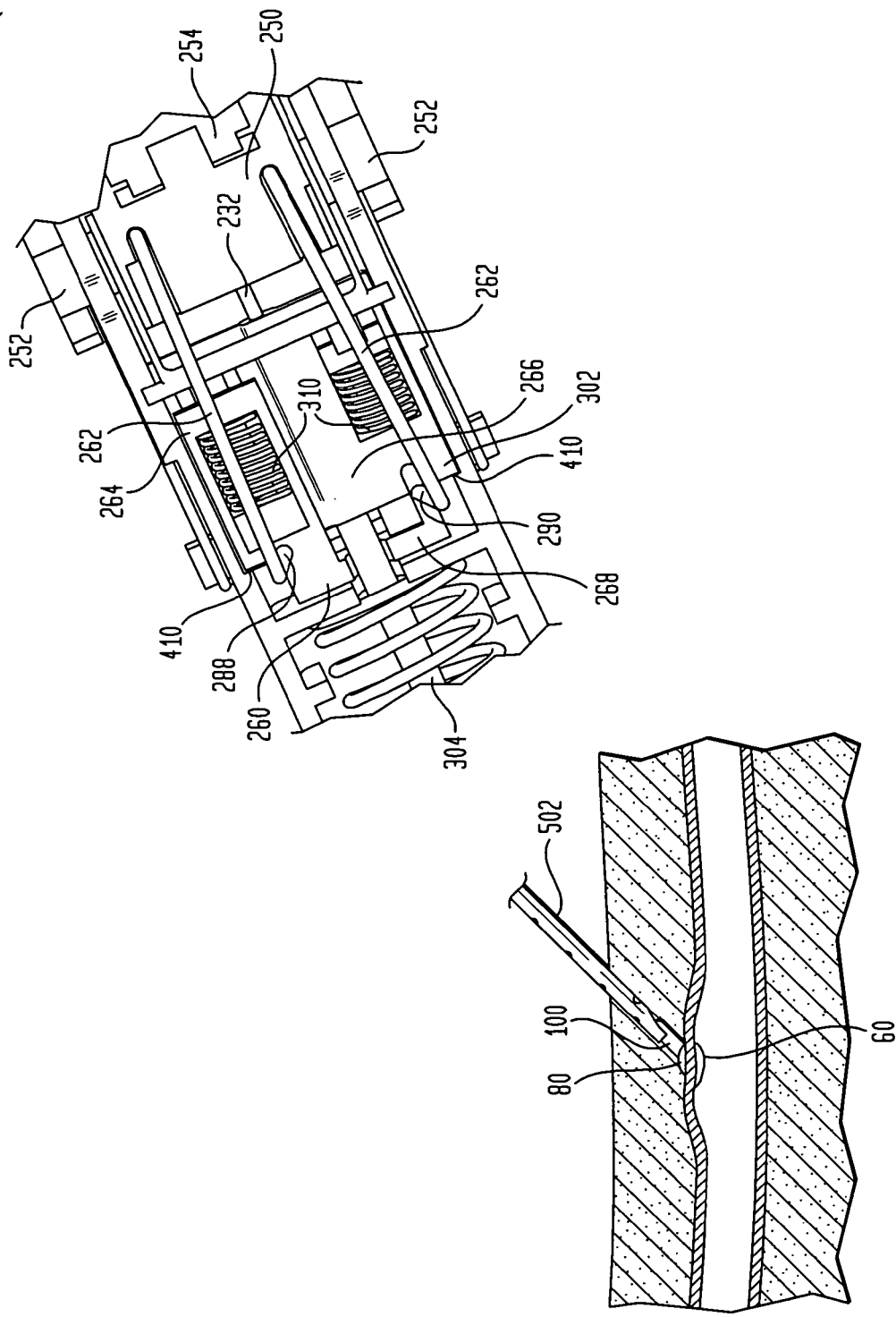

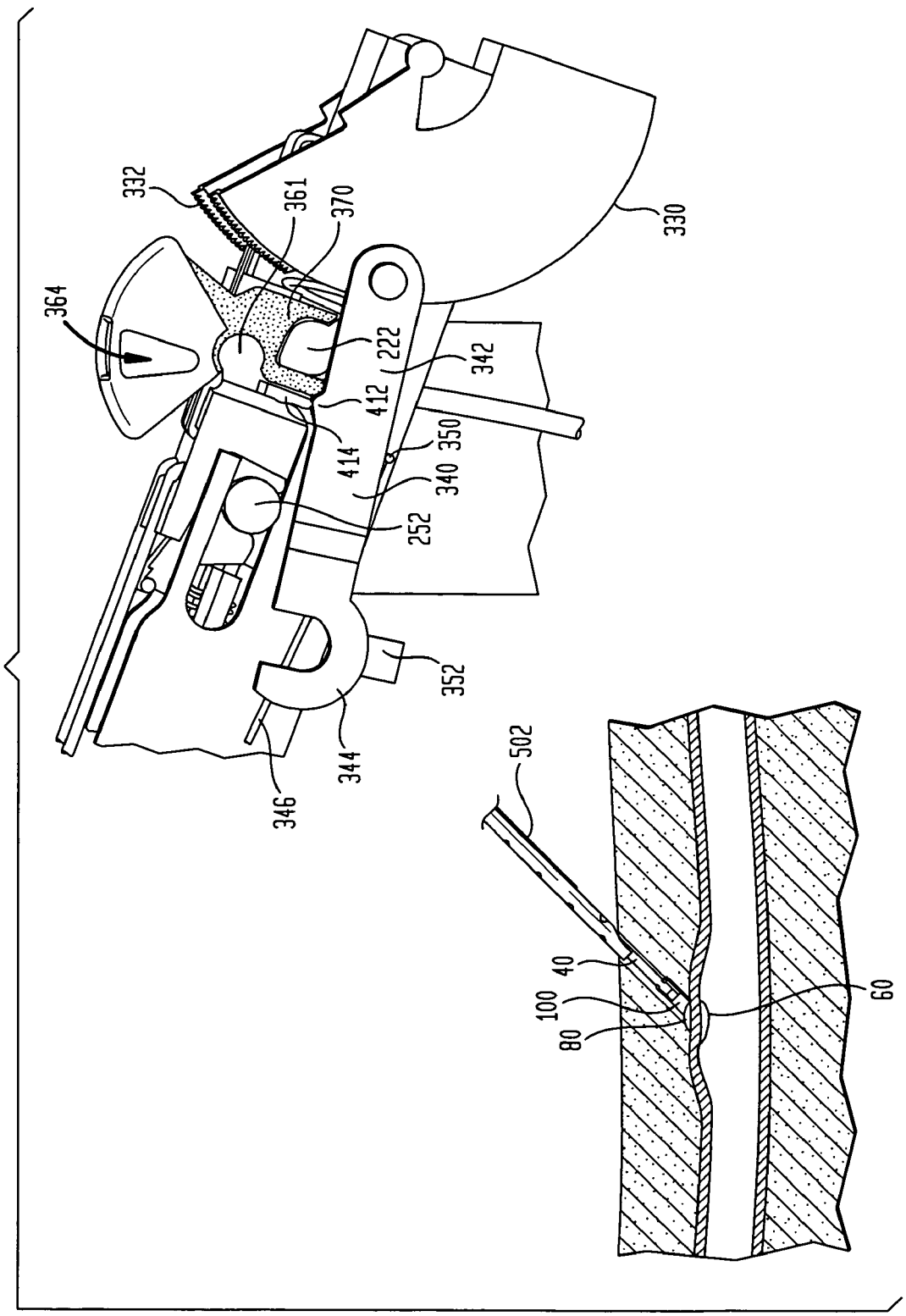

VASCULAR HEMOSTASIS DEVICE AND DEPLOYMENT APPARATUS

CROSS REFERENCE TO RELATED APPLICATIONS

This application claims the benefit of the filing date of U.S. Provisional Application No. 60/920,640, filed on Mar. 29, 2007, the disclosure of which is hereby incorporated by reference herein.

BACKGROUND OF THE INVENTION

The present invention relates to devices for sealing puncture wounds in blood vessels caused by any one of a number of medical procedures, and to methods for sealing such puncture wounds using the device.

In certain medical procedures, such as cardiac catheterization, dilation and counterpulsation, a catheter or other device is inserted in an artery, most commonly by percutaneous methods, and then fed through the arterial tree to the site where needed, frequently, the region of the heart. The site usually selected for insertion is the groin, because the femoral artery in that region is relatively easy to locate.

These procedures are normally initiated by the insertion of an angiographic needle, followed by passing a guide wire through that needle into the artery. The needle is then removed, leaving the guide wire in place. Next, a sheath/dilator set is passed over the guide wire into the artery in order to enlarge the opening sufficiently to permit entry of the catheter or other device. The dilator is then removed leaving the sheath or guide cannula in place. The catheter or other device can then be inserted through the cannula with full confidence that when it emerges from the distal end it will be within the lumen of the artery.

After a procedure, for example, counterpulsation, has been completed, the sheath must be removed and the wound closed. Often, this can be accomplished simply by the application of digital pressure, generally augmented by the use of a conventional pressure dressing, until hemostasis is achieved. Customarily, pressure must be applied for at least one-half hour, and frequently for much longer than that. While pressure dressings often suffice, it is not uncommon for addition devices, such as sand bags, to be needed. In addition, during this period the patient must be immobilized, lest movement interfere with the closing process. Because of the pressure required, the time during which it must be applied and the need for immobilization, the procedure is painful and uncomfortable. It also requires the prolonged personal attention of a healthcare professional. Finally, wound closures accomplished in this matter are prone to reopen unexpectedly long after closure appears to have been completed. Patients are therefore often required to maintain bed rest, oftentimes in the hospital, for 24 hours or longer.

Since sealing can be such a problem, cardiologists tend to use the smallest caliber catheters when performing catheterization procedures. Larger caliber catheters, however, are far preferable. An improved sealing procedure whereby larger catheters can be used without increasing the sealing difficulties would greatly facilitate cardiac catheterization.

SUMMARY OF THE INVENTION

The present invention addresses these needs.

One aspect of the present invention provides a hemostasis device for percutaneously closing a puncture in the wall of a blood vessel. The hemostasis device includes a rigid post having a length; and first and second clamping members mounted on the rigid post. The first clamping member is sized for insertion through the puncture in the wall of the blood vessel and has a first face for engaging an inside surface of the blood vessel adjacent the puncture. The second clamping member is movable along the rigid post toward the first clamping member and has a first face for engaging an outside surface of the blood vessel adjacent the puncture. The first and second clamping members are spaced relatively far apart along the length of the rigid post in an initial collapsed state, and are relatively close together in a deployed state, the wall of the blood vessel being sandwiched between the first and second clamping members in the deployed state. The first clamping member may be mounted to the rigid post so as to be pivotable relative to the rigid post. Moreover, each of the first and second clamping members may have an elongated shape, and the first clamping member may lie substantially orthogonal to the second clamping member in the deployed state.

In one embodiment hereof, the hemostasis device may further include a retaining member for retaining the second clamping member adjacent the outside surface of the blood vessel in the deployed state. The length of the rigid post may include a plurality of teeth, and the retaining member may include at least one pawl for engaging the plurality of teeth, whereby the engagement of the at least one pawl with the plurality of teeth resists movement of the retaining member relative to the rigid post. The rigid post may also include at least one recess at a proximal end thereof, the recess being sized to receive the at least one pawl of the retaining member for holding the retaining member in a fixed position relative to the rigid post in the initial collapsed state.

In another embodiment hereof, the rigid post may include a first portion and a second portion connected in end-to-end relationship so as to define an oblique angle between the first portion and the second portion. The oblique angle may be between about 120° and about 150°, and preferably is about 135°.

In this embodiment of the hemostasis device, the first portion of the rigid post may include a plurality of teeth formed along the length thereof, and the second portion of the rigid post may be devoid of teeth.

In a variant of this embodiment, the first clamping member may include an aperture formed at an acute angle to the first face thereof, the aperture being sized to receive the second portion of the rigid post. The acute angle may be between about 30° and about 60°, and preferably is about 45°. More preferably, the acute angle is complementary to the oblique angle between the first portion and the second portion of the rigid post.

In yet a further embodiment, the first clamping member may have a width and a length greater than the width. In accordance with this embodiment, the first clamping member may have a second surface which is smoothly curved in the length direction and width direction. The rigid post may have an enlarged head at a distal end thereof, with the enlarged head being recessed below the second surface of the first clamping member in the deployed state.

In a still further embodiment, the rigid post may include a substantially linear first portion and a substantially linear second portion, the first portion being axially offset from the second portion in two orthogonal directions to define a shallow recess in the rigid post. The shallow recess may be sized to accommodate one end of the second clamping member in the initial collapsed state.

In highly preferred embodiments, the rigid post and the first and second clamping members are formed from a resorbable material. Preferably, the resorbable material is a polymer, including copolymers of lactide and glycolide.

In still further embodiments, the hemostasis device may include a plate of hemostatic material positioned on the rigid post between the first and second clamping members. The plate of hemostatic material may be connected to the first face of the second clamping member, and may be adhered to the first face of the second clamping member by a biologically compatible adhesive. Preferred hemostatic materials include collagen.

Another aspect of the present invention provides a method for percutaneously closing a puncture in the wall of a blood vessel. The method includes providing a hemostasis device including a rigid post, and first and second clamping members mounted on the rigid post; inserting the rigid post and the first clamping member through the puncture in the wall of the blood vessel; applying tension to the rigid post to urge the first clamping member against an inside surface of the blood vessel adjacent the puncture; and urging the second clamping member along the rigid post toward the first clamping member and into contact with an outside surface of the blood vessel adjacent the puncture.

In a preferred embodiment hereof, the method may further include advancing a retaining member along the rigid post, whereby the advancement of the retaining member urges the second clamping member against the outside surface of the blood vessel.

In a variant of this method, a hemostatic material may be positioned between the outside surface of the blood vessel and the second clamping member.

Yet another aspect of the present invention provides a deployment instrument for deploying a hemostasis device to close a puncture in the wall of a blood vessel, the hemostasis device including a rigid post and first and second clamping members mounted on the rigid post. The deployment instrument includes an elongated housing extending in a longitudinal direction between a proximal end and a distal end. A tensioning system is disposed in the housing and is operable to apply tension to the rigid post. A drive assembly is also disposed in the housing and is operable to urge the second clamping member along the rigid post toward the first clamping member and into contact with an outside surface of the blood vessel.

In one embodiment hereof, the tensioning system may include a hub movable in the longitudinal direction, and a spring operable to bias the hub toward the proximal end of the housing. A tension rod may be connected at one end to the hub and extend along the housing to a free end engageable with the rigid post of the hemostasis device. The housing may include opposed sidewalls, at least one sidewall defining an elongated hub travel slot extending in the longitudinal direction. At least one arm may project laterally from the hub into the hub travel slot, whereby the hub travel slot defines an extent of movement of the hub in the longitudinal direction.

In another embodiment hereof, the drive assembly may include a drive block movable in the longitudinal direction, and a pusher member having a first end and a free end operable to engage the hemostasis device. A coupling assembly may be interposed between the drive block and the pusher member to transmit movement of the drive block in the longitudinal direction to the pusher member. The coupling assembly may have a first condition operable to couple the drive block to the pusher member so that movement of the drive block in the longitudinal direction toward the distal end of the housing causes a corresponding movement of the pusher member in the longitudinal direction. The coupling assembly may also have a second condition operable to decouple the drive block from the pusher member so that movement of the drive block in the longitudinal direction toward the distal end of the housing does not cause a corresponding movement of the pusher member in the longitudinal direction.

In a preferred embodiment hereof, the coupling assembly may include first and second carriage members slidable relative to one another in the longitudinal direction, and at least one rigid drive link operatively connecting the first and second carriage members to the drive block. The first and second carriage members in a first position relative to one another may define a closed aperture capturing the at least one drive link to thereby maintain the drive block at a fixed distance from the coupling assembly. The first and second carriage members in a second position relative to one another may open the closed aperture to release the at least one drive link and thereby enable the drive block to move in the longitudinal direction toward the coupling assembly. The coupling assembly may be spaced from the drive block by a first distance prior to deployment of the hemostasis device, and by a second distance less than the first distance after deployment of the hemostasis device.

In another preferred embodiment hereof, the deployment instrument may further include a lock-out member connected to the drive block for pivotable movement between a first position in which the lock-out member is interposed between the drive block and the carriage assembly to maintain the drive block at a fixed distance from the coupling assembly, and a second position in which the lock-out member is positioned above the coupling assembly to enable the drive block to move in the longitudinal direction toward the coupling assembly. The lock-out member may be urged from the first position to the second position by a cam surface on the housing. The cam surface may be oriented to urge the lock-out member from the first position to the second position as the drive block moves in the longitudinal direction toward the distal end of the housing.

In still another preferred embodiment, the housing may include opposed sidewalls, at least one sidewall defining an elongated drive block travel slot extending in the longitudinal direction. At least one boss may project laterally from the drive block into the drive block travel slot, whereby the drive block travel slot defines an extent of movement of the drive block in the longitudinal direction.

The deployment instrument in accordance with this embodiment may further include an actuator operable to move the drive block in the longitudinal direction toward the distal end of the housing. At least one deployment link may be provided having one end pivotably connected to the actuator and a free end, the free end including a recess sized to receive the at least one boss of the drive block. The actuator may be operable to move the drive block in the longitudinal direction only when the at least one boss of the drive block is positioned within the recess of the at least one deployment link.

In a highly preferred embodiment hereof, at least one of the sidewalls may define an elongated hub travel slot extending in the longitudinal direction, and the hub may include at least one arm projecting laterally from the hub into the hub travel slot, whereby the hub travel slot defines an extent of movement of the hub in the longitudinal direction. Preferably, the actuator is movable through a movement path, and the hub is movable in the longitudinal direction between an initial position in which the at least one arm of the hub is positioned in the movement path of the actuator to prevent the actuator from moving the drive block, and a tension position in which the at least one arm of the hub is positioned outside of the movement path of the actuator to permit the actuator to move the drive block. More preferably, the hub is moved to the tension position when the tensioning system applies a predetermined tension to the rigid post. The movement of the hub from the initial position to the tension position may move the coupling assembly in the longitudinal direction toward the distal end of the housing. When the hub is in the tension position, the recess of the at least one deployment link may be aligned to receive the at least one boss of the drive block.

In one variant of this embodiment, the deployment instrument may further include a locking mechanism operable to prevent the actuator from moving the drive block when less than the predetermined tension is applied to the rigid post. In accordance with such variant, the actuator may include a plurality of teeth, and the at least one arm of the hub may include a pawl. The pawl may engage the plurality of teeth when less than the predetermined tension is applied to the rigid post to prevent the actuator from moving the drive block.

In another variant hereof, the pusher member may include an elongated bore, and the tension rod may be slidably disposed in the elongated bore. The hub and the coupling assembly may be operatively linked so that there is substantially no relative movement between the tension rod and the pusher member as the hub is moved from the initial position to the tension position. Preferably, movement of the drive block relative to the hub in the distal direction of the housing causes the pusher member to move in the distal direction relative to the tension rod to thereby urge the second clamping member along the rigid post toward the first clamping member and into contact with the outside surface of the blood vessel.

BRIEF DESCRIPTION OF THE DRAWINGS

A more complete appreciation of the subject matter of the present invention and the various advantages thereof can be realized by reference to the following detailed description, in which reference is made to the accompanying drawings in which:

FIG. 1 is an enlarged, schematic cross-sectional view of one type of insertion site, showing a balloon catheter having passed over a guide wire through an insertion sheath into the femoral artery of the patient;

FIG. 2 is a perspective view of the hemostasis device of the present invention in an initial collapsed state;

FIG. 3A is a front elevational view of the rigid post of the hemostasis device of FIG. 2;

FIG. 3B is a side elevational view of the rigid post shown in FIG. 3A;

FIG. 4 is a side elevational view of the foot of the hemostasis device of FIG. 2;

FIG. 5A is a perspective view of the seal of the hemostasis device of FIG. 2;

FIG. 5B is a plan view of the seal shown in FIG. 5A;

FIG. 6 is a perspective view of an alternate embodiment of the hemostasis device of the present invention incorporating a plate of hemostatic material;

FIG. 8A is a perspective view showing the hemostasis device of FIG. 2 loaded in a transfer sleeve;

FIG. 8B is an enlarged detailed view of FIG. 8A showing the connection of the tension rod of the deployment instrument to the hemostasis device;

FIG. 9A is an exploded view of the puller/pusher carriage used in the deployment instrument of FIG. 7;

FIG. 9B is an assembled perspective view of the puller/pusher carriage of FIG. 9A;

FIGS. 10A-10C are highly schematic partial cross-sectional views showing the sequence of steps to connect the deployment instrument to an insertion sheath in accordance with the present invention;

FIGS. 12A-12H are highly schematic partial cross-sectional views showing the sequence of steps to seal a puncture wound in a blood vessel using the hemostasis device shown in FIG. 2, the views showing both the condition of the deployment instrument and the corresponding position of the hemostasis device at each step in the sequence.

DETAILED DESCRIPTION

Figure 7:
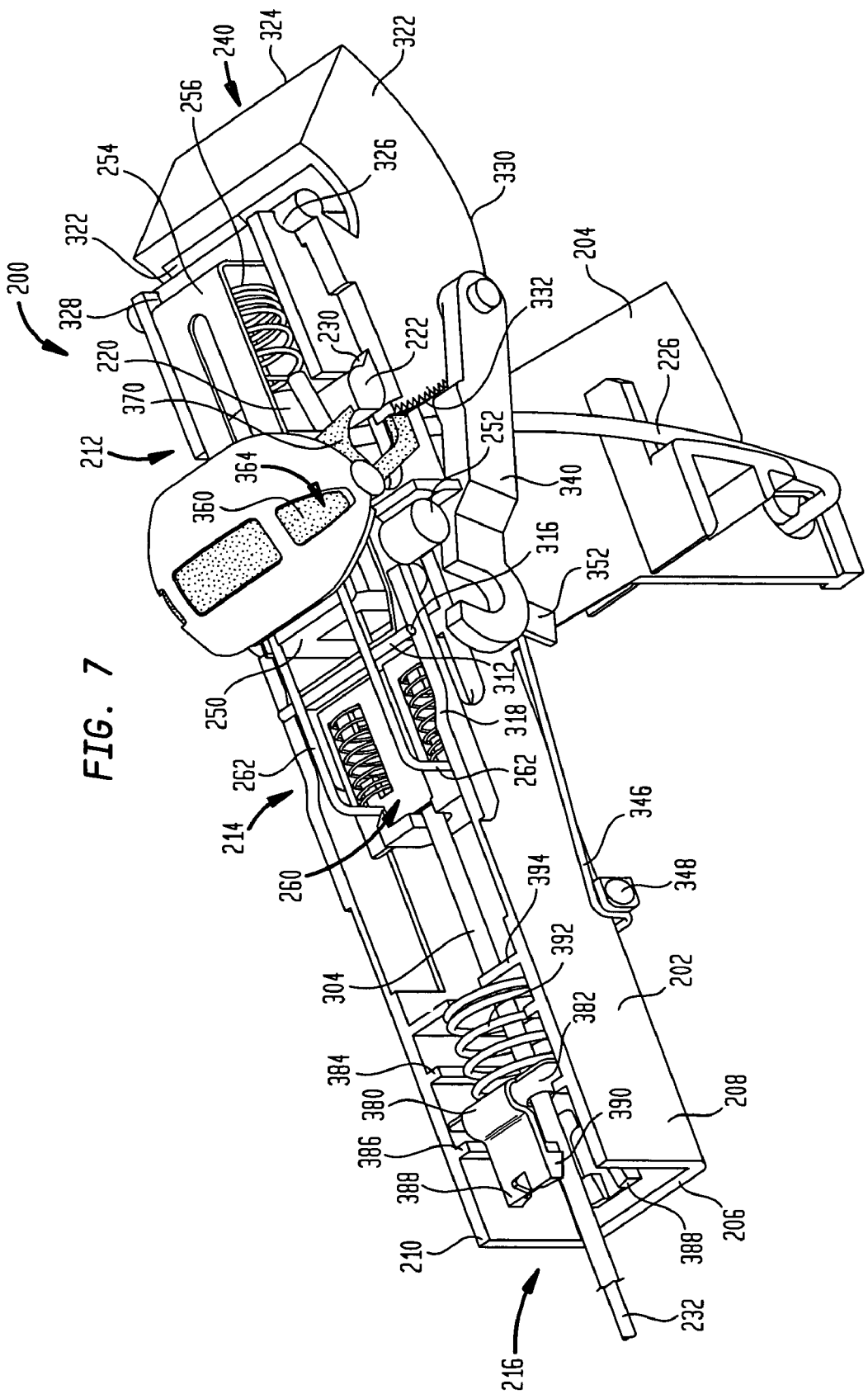
FIG. 7 is a highly schematic perspective view of a deployment instrument for deploying the hemostasis devices of the present invention.

In certain procedures, for example, intra-aortic balloon pumping ("IABP"), percutaneous transluminal coronary angioplasty ("PTCA") and angiography, as best seen in FIG. 1, a catheter or other medical device 10 is inserted into a blood vessel or artery 16, typically using what is commonly known as the Seldinger technique. In accordance with this technique, a hollow needle (not shown) is inserted through the skin into the blood vessel or artery 16, most frequently the common femoral artery in the groin area of the patient's leg 20, thereby creating a puncture wound 14. Puncture wound 14 includes a tissue channel 18 extending through a layer of tissue separating blood vessel 16 from the patient's skin. A guide wire 22 is then inserted through the needle and advanced to the desired area. Keeping the guide wire 22 in place, the needle is removed and discarded. A dilator/insertion sheath set is then advanced over the guide wire and inserted into the blood vessel to dilate the puncture wound, following which the dilator is removed, leaving the insertion sheath 24 in place in the puncture wound. The catheter or other medical device 10 is then inserted through the insertion sheath 24 and into the blood vessel 16 to perform the desired medical procedure. When the medical procedure has been completed, the catheter or other such device, the guide wire and the introducer sheath must be removed and the puncture wound closed. Although puncture wounds of the sort made by percutaneous procedures will generally, after removal of all sheaths and catheters, be in the nature of slits, for ease of understanding, they are depicted in the drawings herein more as holes. The shape of the puncture wound, however, is not critical.

It should be understood that the subject invention is independent of the nature of the medical device being used to treat the patient. Accordingly, the term "catheter" is used herein in a very generic and broad way to include not only "catheters" in the strict sense, but any device that is inserted into the body.

Similarly, the subject invention is independent of whether a particular blood vessel is involved, and if so, which blood vessel. While it is anticipated that the femoral artery will be the most commonly used blood vessel for many percutaneous procedures, other arteries as well as veins might just as easily be involved.

Hemostasis Device

The present invention employs a hemostasis device 30, as shown in FIG. 2, for sealing puncture wound 14. In accordance with the method of the invention, after a medical procedure has been completed, a conventional catheter or sheath exchange is effected by which the insertion sheath 24 used for the medical procedure is removed from the tissue channel and replaced with a sheath 500. A deployment instrument 200 having a hemostasis device 30 loaded therein is connected to sheath 500 and manipulated to deploy the hemostasis device and thereby close the puncture wound through the blood vessel wall. A detailed description of deployment instrument 200 and the method of using same to deploy hemostasis device 30 are set forth below.

Hemostasis device 30 has four main components, namely, a rigid post 40, a foot 60 pivotally disposed at the distal end of post 40, a seal 80 slidably mounted on rigid post 40, and a locking ratchet 100 also slidably mounted on post 40 proximally of seal 80. Each of these components is preferably formed by injection molding a resorbable medical grade polymer. Preferred polymers in this regard include polyglycolic acid (PGA) and its copolymers including polylactic glycolic acid (PGLA) and combinations thereof. A 50:50 copolymer of lactide and glycolide is highly preferred for rigid post 40 and seal 80, while an 85:15 copolymer of lactide and glycolide is highly preferred for foot 60 and ratchet 100. Particularly preferred polymers are Resomer™ lactide-glycolide copolymers available from Boehringer-Ingelheim Chemicals, Inc. of Petersburg, Va. A detailed description of each of the components of hemostasis device 30 follows.

Rigid post 40 includes a substantially linear elongated portion 42 having a square or rectangular cross-section. A series of serrations or teeth 44 may be formed on one or opposite sides of portion 42 along the length thereof. Teeth 44 need not be formed at the proximal end of rigid post 40, as will be appreciated from discussions later herein.

At its proximal end, portion 42 may include a pair of recesses 46 on opposite sides thereof, and spaced from teeth 44. Recesses 46 receive the pawls of ratchet 100, described below, and hold the ratchet securely in place in the initial collapsed condition of hemostasis device 30. A further recess 48 may be formed on one side of portion 42 proximally of recesses 46. The proximal wall 48a of recess 48 may be tapered to mate with a portion of deployment instrument 200 having a complementary taper, the purpose of which is described below. Alternatively, recess 48 may be formed without a tapered proximal wall 48a. In such event, the complementary portion of deployment instrument 200 may or may not be tapered.

At its distal end, portion 42 has a non-serrated extension 50 formed at an oblique angle thereto. Preferably, the angle between extension 50 and portion 42 corresponds to the angle at which the needle used in the Seldinger technique of catheter insertion enters the blood vessel. Typically, this is between about 30° and about 60°, and nominally about 45°, to the longitudinal direction of the blood vessel. Therefore, the angle between extension 50 and portion 42 is preferably between about 120° and about 150°, and most preferably about 135°. Extension 50 also may be formed with a square or rectangular cross-section, and has an enlarged nub 52 at its free end.

Although elongated portion 42 of rigid post 40 is described above as being substantially linear, that is not necessarily the case. Rather, portion 42 may include two substantially linear portions 42a and 42b which are axially offset from one another by a small amount in two orthogonal directions. That is, referring to FIG. 3B, portion 42a may be axially offset from portion 42b in the direction of extension 50. This offset creates a shallow recess 54 for accommodating one end of foot 60 in the initial collapsed state of hemostasis device 30. Similarly, referring to FIG. 3A, portion 42a may be offset from portion 42b by a small amount in a direction orthogonal to the first offset direction. This offset creates a shallow recess 56 which accommodates one end of seal 80 in the initial collapsed state of hemostasis device 30. Thus, by defining shallow recesses 54 and 56, the compound offsets formed in portion 42 of rigid post 40 enable the cross-sectional profile of hemostasis device 30 in the initial collapsed state to be minimized, thereby facilitating its deployment endovascularly.

Foot 60 has an elongated, generally elliptical plan profile with a substantially planar first surface 62 and a second surface 64 which may be smoothly curved in both the lengthwise and widthwise directions. Near its center, foot 60 includes a square or rectangular aperture 66 which is sized and shaped to receive the extension 50 of rigid post 40. As can be seen in FIG. 4, aperture 66 is formed at an oblique angle to planar surface 62. Preferably, the oblique angle at which aperture 66 is formed is complementary to the angle between portion 42 and extension 50 of rigid post 40 (i.e., together the angles define a straight line). Thus, aperture 66 preferably is formed at an angle of between about 30° and about 60° to planar surface 62; with an angle of about 45° being most preferred. Curved surface 64 may have a first wall 68 tapered at a first angle to planar surface 62 and a second wall 70 tapered at a shallower angle to planar surface 62. Collectively, walls 68 and 70 define a notch 72 in curved surface 64 for accommodating the enlarged nub 52 at the distal end of rigid post 40. Notch 72 enables nub 52 to lie substantially below curved surface 64 of foot 60 in the fully deployed condition of hemostasis device 30.

It was noted above that aperture 66 has a shape which corresponds to the cross-sectional shape of extension 50. This shape correspondence prevents foot 60 from rotating on rigid post 40. Moreover, making aperture 66 slightly larger in size than the cross-sectional size of extension 50 provides for a small degree of pivoting movement between foot 60 and rigid post 40.

Seal 80 also has a generally elliptical plan profile with a substantially planar first surface 82 and a second surface 84 which may be smoothly curved both in the lengthwise and widthwise directions. A substantially rectangular aperture 86, offset from both the lengthwise and widthwise center lines of the seal, is sized and shaped to slidably receive portion 42 of rigid post 40. As can be seen in the plan view of FIG. 5B, aperture 86 is formed at an oblique angle to planar surface 82 in the longitudinal direction of seal 80, and at an oblique angle to a plane passing through the longitudinal center line of the seal.

As noted above, aperture 86 has a generally rectangular cross-section. However, aperture 86 is enlarged in the longitudinal direction at one corner thereof to define a notch 92. As a result of this enlargement and the overall shape of aperture 86, the exertion of downward pressure pushing seal 80 along rigid post 40 causes the seal to rotate to an orientation substantially orthogonal to the orientation of foot 60.

Hemostasis device 30 also may include a locking ratchet 100 assembled on rigid post 40 in a position proximal of seal 80. Referring to FIG. 2, locking ratchet 100 has an annular member 102 which defines a generally square aperture for slidably receiving portion 42 of rigid post 40. A pair of opposed arms 104 project in a cantilevered fashion from annular member 102. Each arm includes an inwardly projecting pawl 108 at its free end adapted to engage the teeth 44 on rigid post 40. The interaction of pawls 108 with teeth 44 is such that locking ratchet 100 may slide in a distal direction along rigid post 40, but is prevented from sliding in a proximal direction thereon.

Referring back to FIG. 2, each of foot 60, seal 80 and locking ratchet 100 are assembled on rigid post 40 in the initial collapsed state of hemostasis device 30. In this initial state, foot 60 is pivoted on extension 50 so that it approaches a parallel orientation relative to portion 42, with one end of foot 60 lying substantially within recess 54, thereby minimizing the cross-sectional profile of hemostasis device 30. Similarly, seal 80 in the initial collapsed state of hemostasis device 30 is pivoted on rigid post 40 until it is at an acute angle relative to the post. In this pivoted position, one end of seal 80 resides within recess 56, again minimizing the cross-sectional profile of hemostasis device 30 in the collapsed state. The entire foot 60 and the entire seal 80 pivot relative to the rigid post 40.

In the initial collapsed state of hemostasis device 30, seal 80 preferably is positioned near the beginning of teeth 44 at a position spaced from foot 60. Further, locking ratchet 100 preferably is positioned on rigid post 40 just proximally of seal 80. Locking ratchet 100 may be held securely in this position and prevented from prematurely sliding proximally on rigid post 40 by the engagement of pawls 108 of the locking ratchet within recesses 46. A transfer sleeve 400 (see FIG. 8A) may hold hemostasis device 30 in this collapsed state until the hemostasis device is ready for deployment.

In an alternate embodiment shown in FIG. 6, hemostasis device 30 optionally may include a collagen plate 110 positioned distally of seal 80. Collagen plate 110 may be attached to surface 82 of seal 80 using any known biologically compatible adhesive. Alternatively, collagen plate 110 simply may be positioned adjacent surface 82 of seal 80, but not attached thereto. Rather than collagen, plate 110 may be formed from any material that will promote hemostasis at the site of puncture wound 14.

It will be appreciated that various modifications may be made to hemostasis device 30 pursuant to the present invention. In one variant, for example, the elongated portion 42 of rigid post 40 may be formed without teeth 44 along the majority of its length. Rather, one or more teeth 44 may be formed on opposite sides of portion 42 near its distal end. In such event, seal 80 and ratchet 100 may be assembled on rigid post 40 with a friction fit. Preferably, sufficient friction would be created to hold seal 80 and ratchet 100 in place during the assembly and transport of hemostasis device 30, and during the initial deployment of same. The one or more teeth 44 at the distal end of portion 42 would be sufficient to hold seal 80 and ratchet 100 in place at the completion of deployment.

In another variant, rigid post 40 need not have a square or rectangular cross-section. In that regard, rigid post 40 may have an elliptical, triangular or hexagonal cross-section, or any other cross-sectional shape which will prevent foot 60 and locking ratchet 100 from rotating on the rigid post, and which will prevent seal 80 from rotating in an uncontrolled manner as it advances along the length of the rigid post. It is further contemplated that portion 42 and extension 50 of rigid post 40 may have the same or different cross-sectional shapes. In either event, aperture 66 in foot 60 preferably has a shape which is complementary to the cross-sectional shape of extension 50 so as to prevent foot 60 from rotating thereon. Similarly, the shapes of aperture 86 in seal 80 and the aperture in ratchet 100 are preferably complementary to the cross-sectional shape of portion 42 of rigid post 40 so as to prevent ratchet 100 from rotating on portion 42 and seal 80 from rotating in an uncontrolled manner on portion 42.

In still another variant, rigid post 40 need not include recess 48 for engaging a complementary portion of deployment instrument 200. Rather, the proximal end of rigid post 40 may be formed with an eyelet sized to receive a length of suture. The suture may then be used to hold hemostasis device 30 in assembled relationship to deployment instrument 200 during deployment of hemostasis device 30, and may simply be pulled from the eyelet following the deployment procedure. Moreover, the present invention contemplates any known means for engaging rigid post 40 to deployment instrument 200 in a manner that provides for the quick and ready release of the hemostasis device 30 following deployment.

Deployment Instrument

A deployment instrument 200 for positioning hemostasis device 30 at the puncture wound in blood vessel 16 and for deploying the hemostasis device to close the puncture wound is illustrated in FIG. 7. Deployment instrument 200 is shown in FIG. 7 and in the other figures herein with its outer shroud or housing removed so that the various internal components of the deployment instrument and their operation can be readily seen. The deployment instrument has a generally pistol-shaped configuration including an elongated housing in the form of barrel 202 and a hand grip 204. Barrel 202 is formed by a bottom 206 and a pair of sidewalls 208 and 210, and houses both a tensioning system 212 for applying controlled tension to hemostasis device 30 during deployment, and a ratchet drive assembly 214 operable to drive locking ratchet 100 and, along with it, seal 80, distally along rigid post 40 during such deployment. For purposes of the following description, the end of deployment instrument 200 having hand grip 204 will be referred to as the rear or proximal end, and to move in the proximal direction, proximally or rearwardly will refer to movement in the direction of the hand grip. The free end 216 of barrel 202 will be referred to as the front or distal end of the deployment instrument, and to move in the distal direction, distally or forwardly will refer to movement in the direction of free end 216.

Tensioning system 212 includes a tensioning hub 220 movable longitudinally within barrel 202 and having a pair of arms 222 (only one of which is visible in the figures) projecting laterally from the opposite sides thereof so as to protrude outwardly of the sidewalls 208 and 210 of barrel 202. Arms 222 reside and travel within cutouts 224 formed in sidewalls 208 and 210. Thus, the length of cutouts 224 defines the extent of movement of hub 220 in the proximal and distal directions within barrel 202. Hub 220 is biased in the proximal direction by U-shaped tension spring 226, the middle of which is connected to hand grip 204, and the free ends of which engage arms 222. The free end of each arm 222 includes a proximally directed pawl 230 which interferes with the movement of trigger 240 and prevents it from being actuated prematurely.

A tension rod 232 is fixedly connected at one end to hub 220, and extends beyond the end 216 of barrel 202 to a free end 234. A recess 236 maybe formed at a spaced distance from free end 234 so as to define an end portion 238 sized for receipt in recess 48 on the rigid post 40 of hemostasis device 30. More particularly, wall 236a of recess 236 preferably has a complementary taper to the taper of wall 48a of recess 48 so that end portion 238 may mate within recess 48.

Ratchet drive assembly 214 includes a drive block 250 positioned distally of tensioning hub 220 and movable in the longitudinal direction within barrel 202. Drive block 250 has a pair of bosses 252 which project laterally from the opposite sides thereof so as to protrude outwardly from the sidewalls 208 and 210 of barrel 202. A U-shaped bracket 254 is connected at its free ends to the top and bottom of drive block 250, and projects proximally therefrom beyond tensioning hub 220. A spring 256 interposed between hub 220 and bracket 254 biases drive block 250 proximally toward hub 220.

A puller/pusher carriage 260 is positioned distally of drive block 250 and is connected thereto by a pair of drive links 262. Referring to FIGS. 9A and 9B, puller/pusher carriage 260, which also is movable longitudinally within barrel 202, is formed from two components, a lower carriage member 264 and an upper carriage member 266. Lower carriage member 264 has a generally rectangular plan profile with a front wall 268, a top wall 270 extending proximally from the top of the front wall and outwardly thereof so as to define a notched corner 272, and an intermediate wall 274 extending proximally and outwardly from the front wall at a spaced distance below the top thereof so as to define a notched corner 276. The top wall includes a slot 278 having a pair of opposed bosses 280 at either end thereof. In a similar fashion, the intermediate wall 274 includes a slot 282 having a pair of opposed bosses 284 at either end thereof. The top wall 270 is spaced from the intermediate wall 274 so as to define an elongated opening 286 therebetween. An angled slot 288 is formed in top wall 270 inwardly from notched corner 272, and another angled slot 290 is formed in intermediate wall 274 inwardly from notched corner 276.

Upper carriage member 266 has an elongated central spine 292 with a pair of generally flat wings 294 extending laterally from the opposite sides thereof. Each wing 294 includes an elongated slot 296 having a pair of opposed bosses 298 at either end thereof. A slot 300 extending proximally from the front edge of each wing defines a tab 302 on each wing which projects forwardly of the front edge of the wing. Wings 294 need not lie in a single plane on opposite sides of spine 292. Rather, one wing 294a may be displaced upwardly on spine 292 and the other wing 294b may be displaced downwardly on spine 292 so that the wings lie on opposite sides of a horizontal plane passing through the center of the spine.

Upper carriage member 266 is assembled to lower carriage member 264 so that wing 294b lies below top wall 270 and wing 294a lies above intermediate wall 274. In this assembled position, the opposed bosses 298 of upper carriage member 266 will be aligned with the opposed bosses 280, 284 of lower carriage member 264, and the slots 300 in upper carriage member 266 will be aligned with the closed ends of slots 288 and 290 in lower carriage member 264.

A tubular ratchet pusher 304 has one end fixedly connected to upper carriage member 266, and extends beyond the end 216 of barrel 202 to a free end 306. Preferably, ratchet pusher 304 extends entirely through upper carriage member 266 to the rear edge thereof. Free end 306 is formed with a pair of fingers 308 sized and shaped to mate with ratchet 100, as shown in FIG. 8A and described more fully below. The inner lumen of ratchet pusher 304 has a diameter sufficient to slidingly receive tension rod 232. Thus, in the assembled condition of deployment instrument 200, tension rod 232 extends from tensioning hub 220 and through ratchet pusher 304, with the free end 234 of the tension rod positioned proximally of the free end 306 of the ratchet pusher.

The assembly of upper carriage member 266 to lower carriage member 264 allows sliding movement therebetween in the longitudinal direction of barrel 202. A pair of springs 310 assembled over bosses 280, 298 and 284, 298 bias upper carriage member 266 toward a position in which the front edges of wings 294 contact the front wall 268 of lower carriage member 264.

The drive links 262 which connect puller/pusher carriage 260 to drive block 250 have a generally U-shape consisting of two elongated legs with a connecting member therebetween. The free end of one elongated leg is connected to the top of drive block 250 and the free end of the other elongated leg is connected to the bottom of drive block 250. In the initial condition of deployment instrument 200, shown in FIG. 7, the connecting member of one drive link 262 is captured at the closed end of slot 288 by one tab 302 of upper carriage member 266, and the connecting member of the other drive link 262 is captured at the closed end of slot 290 by the other tab 302 of upper carriage member 266.

A safety lock-out 312 for preventing the premature actuation of the ratchet drive mechanism is interposed between drive block 250 and puller/pusher carriage 260. Safety lockout 312 is pivotally connected to the bosses 252 on either side of drive block 250, and includes a downwardly projecting tab 314 (see FIG. 12E) which, in the initial condition of deployment instrument 200, resides behind spine 292 of upper carriage member 266. A pair of bosses 316 projecting from either side of safety lock-out 312 rest on the upper edges of sidewalls 208 and 210 of barrel 202. Sidewalls 208 and 210 each include an inclined surface 318 such that, as safety lock-out 312 is moved a sufficient distance distally along barrel 202, inclined surfaces 318 will cause safety lock-out 312 to pivot upwardly until tab 314 is clear from spine 292.

Ratchet drive assembly 214 is actuated using trigger 240 to drive locking ratchet 100 to a seated position. Trigger 240 may have a pair of spaced arms 322 joined by a transverse member 324, with one arm 322 pivotally connected to sidewall 208 at pivot point 326, and the other arm 322 pivotally connected to sidewall 210 at pivot point 328. Each arm 322 may have an arcuate edge 330, a portion of which includes a series of serrations 332. As will be described more fully below, if sufficient tension is not maintained on hemostasis device 30 during the deployment procedure, pawl 230 will engage serrations 332 and prevent further movement of trigger 240, thereby preventing full deployment of ratchet 100 and seal 80.

Trigger 240 further includes a deployment link 340 pivotally connected to each of arms 322. Each deployment link 340 has an elongated arm 342 with a U-shaped catch 344 at the free end thereof. Deployment links 340 are biased upwardly against bosses 252 of drive block 250 by a generally U-shaped tension spring 346. The middle portion of tension spring 346 is connected to the bottom 206 of barrel 202, and is bent upwardly on either side of the barrel and over nubs 348 protruding from the sidewalls 208 and 210 of the barrel. The legs of spring 346 extend proximally toward deployment links 340, and terminate in outwardly directed free ends 350 which engage the deployment links on the bottom edges of arms 342. A tab 352 projecting downwardly from the U-shaped catch 344 on each deployment link 340 may hold the legs of spring 346 in place against sidewalls 208 and 210, thereby preventing them from becoming disengaged from the deployment links.

Although trigger 240 has been described above, it will be appreciated that those features described are internal to the outer housing of deployment instrument 200. Thus, although not shown in the figures, deployment instrument 200 may include an external trigger preferably above the proximal end of barrel 202. This external trigger would interact with trigger 240 in a known manner so that manipulation of the external trigger would result in a corresponding actuation of trigger 240.

Deployment instrument 200 may include a safety indicator 360 for indicating when sufficient tension has been applied to hemostasis device 30 to actuate trigger 240 and drive ratchet 100 to its seated position. Indicator 360 may be pivotally connected to both sidewalls 208 and 210, as at pivot point 361 on sidewall 208, and have "go/no go" indicia 366 and 368 visible through a window 364 overlying indicator 360 or formed in the housing or shroud (not shown) covering barrel 202 and hand grip 204. The "go/no go" indicia may consist of two different colors, such as red for "no go" and "green" for "go"; words, such as "yes" or "go" for the "go" condition and "no" or "no go" for the "no go" condition; or symbols, such as a thumbs up symbol for the "go" condition and a thumbs down symbol for the "no go" condition. The lower portion of indicator 360 extending below pivot point 361 (and below the corresponding pivot point (not shown) on sidewall 210) may include a catch 370 having an opening in the proximal direction sized to receive an arm 222 of tensioning hub 220.

At its distal end, barrel 202 may include a free-floating catch 380. Catch 380 has a generally flat body 382 which is movable longitudinally in barrel 202 between a first pair of ribs 384 and a second pair of ribs 386. A pair of resiliently displaceable fingers 388 project distally from body 382, each finger terminating in a catch member 390. Catch 380 is biased in the distal direction against ribs 386 by a spring 392 interposed between body 382 and a transverse wall 394 connected between sidewalls 208 and 210.

Deployment instrument 200 preferably is supplied for use with a hemostasis device 30 already assembled thereto. In a preferred arrangement, shown in FIGS. 8A and 8B, a hemostasis device 30 is assembled to tension rod 232 by mating end portion 238 thereof with recess 48 on rigid post 40 of the hemostasis device 30. This assembly may then be slid into ratchet pusher 304 until the fingers 308 at the free end 306 of the ratchet pusher are seated in the notches 106 between the arms 104 of ratchet 100.

A transfer sleeve 400 may be assembled over hemostasis device 30 and the distal end of ratchet pusher 304 to help maintain the assembled relationship of these components and to protect hemostasis device 30 during shipment. Transfer sleeve 400 preferably has a diameter sufficient for easy sliding movement of hemostasis device 30 and ratchet pusher 304 therein. An enlarged annular rim 402 provided on the proximal end of transfer sleeve 400 may have a seal 404 to prevent the leakage of blood or other body fluids around ratchet pusher 304.

Figure 10A:
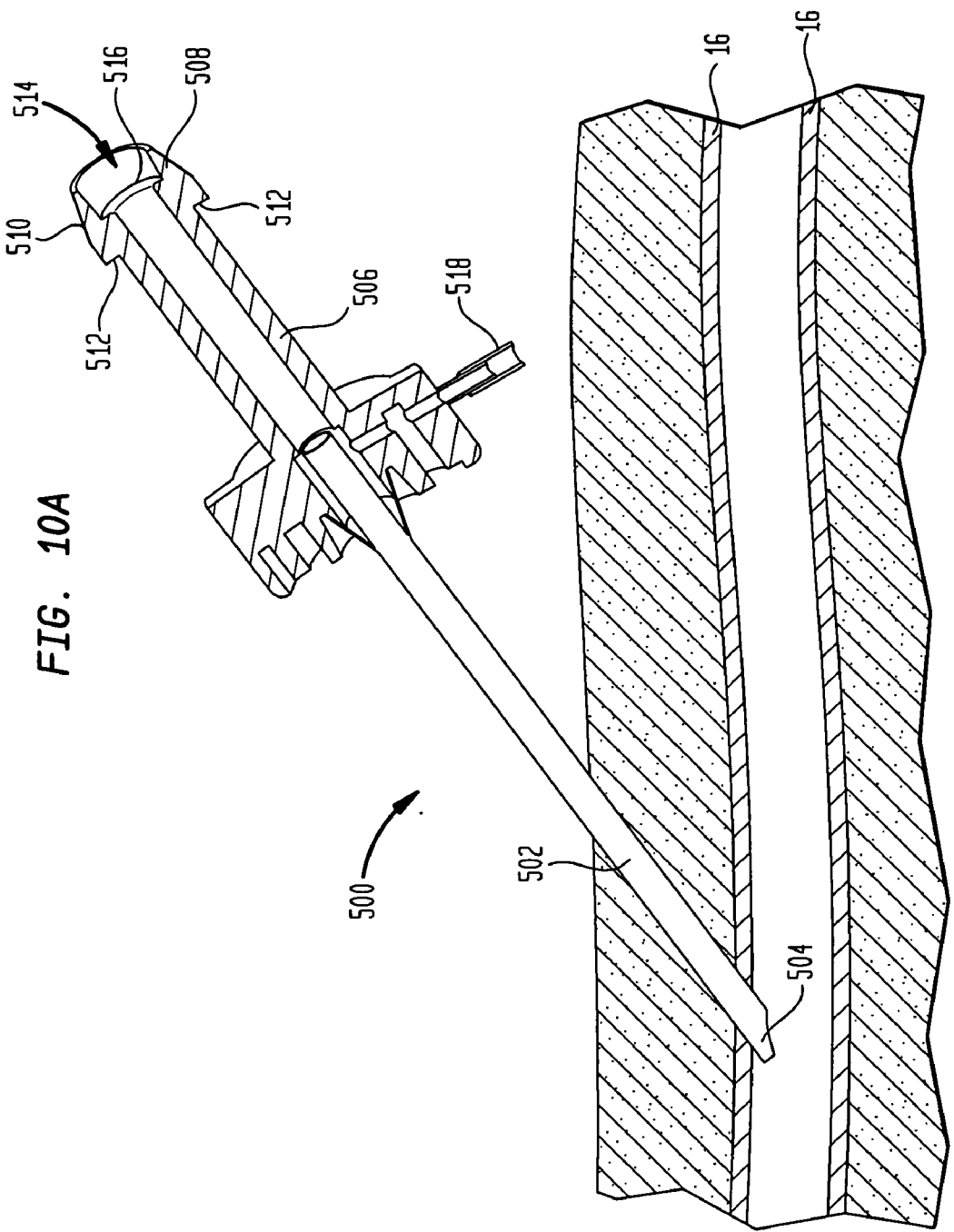
Figure 10C:
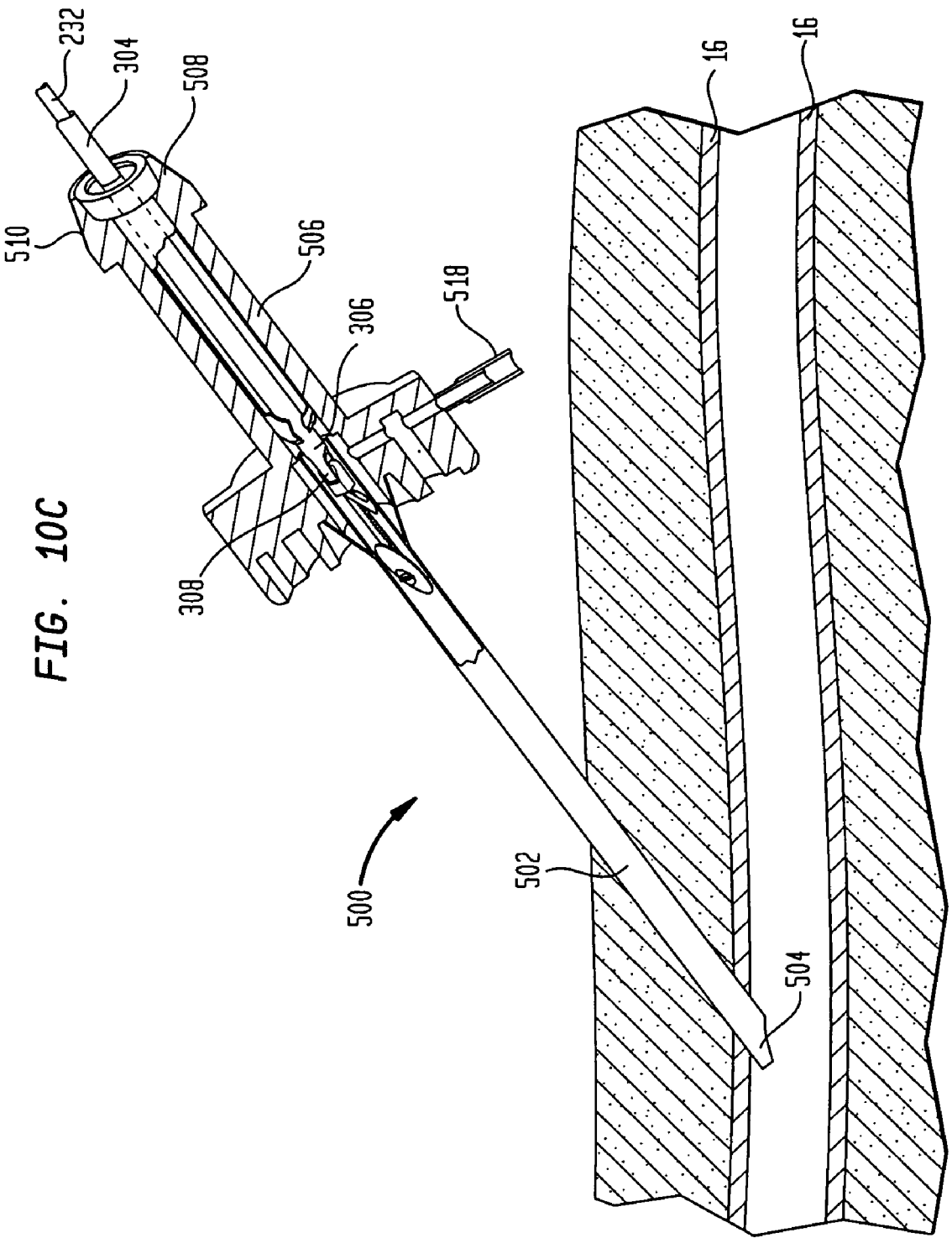
Figure 11:
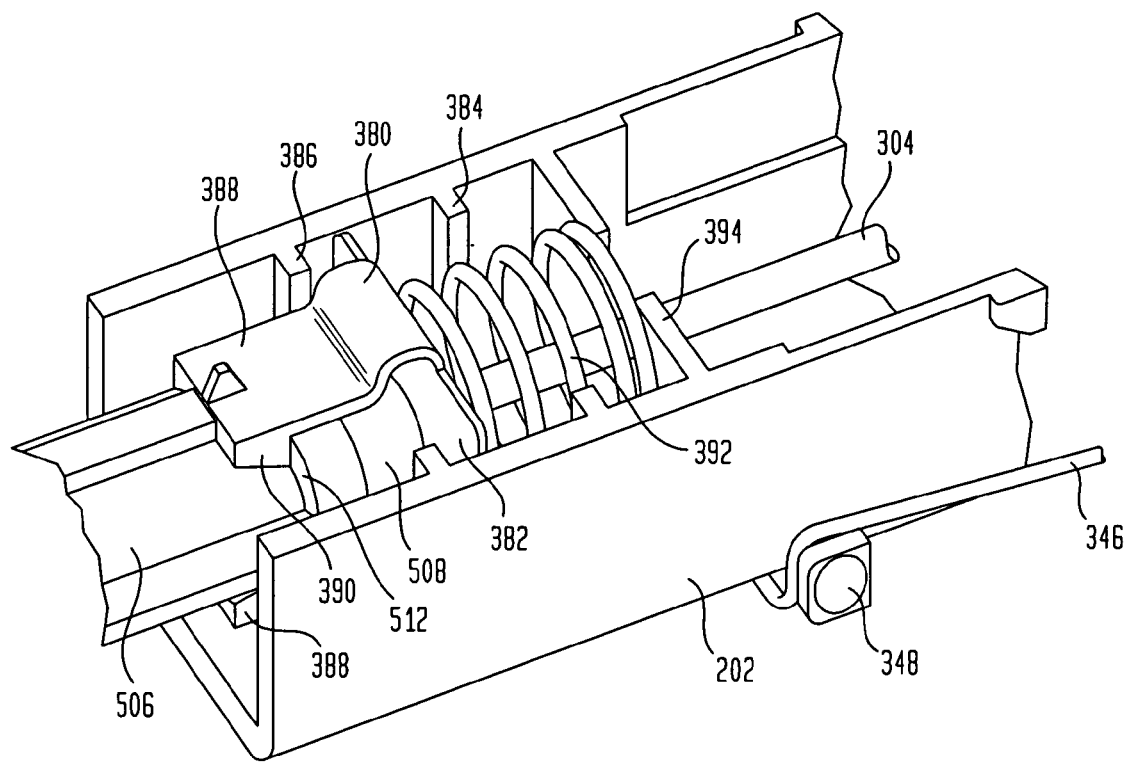
FIG. 11 is an enlarged partial perspective view showing the connection between the insertion sheath and the deployment instrument.

The following will describe, with reference to FIGS. 10-12, the procedure for positioning hemostasis device 30 in blood vessel 16 and for deploying the hemostasis device to close the puncture wound 14 therein. As noted earlier, the procedure is commenced after an interventional procedure has been completed, with the insertion sheath 24 for performing the interventional procedure remaining in place in the puncture wound. Referring to FIG. 10A, the procedure begins with a conventional sheath exchange in which the insertion sheath 24 is removed and a new insertion sheath 500 for deploying hemostasis device 30 is inserted in its place. Sheath 500 includes a cannula 502 having a length sufficient to extend from outside the patient's body through puncture wound 14 and into blood vessel 16. At its distal end, cannula 502 is formed with a collapsed tip 504 which can open as hemostasis device 30 is expelled from the cannula, but which, once hemostasis device 30, and particularly foot 60, has been expelled, prevents the withdrawal of same back through the tip and into the cannula. At its proximal end, cannula 502 is mated with a hub 506 including a connector 508 formed with a conically tapered surface 510 and a wall 512 oriented substantially orthogonal to the longitudinal direction of cannula 502 for mating with catch members 390. Connector 508 may be provided with an annular recess 514 defining an annular wall 516 at a spaced distance from the free end of the connector. A seal (not shown) may be provided in connector 508 to prevent the leakage of blood or other body fluids traveling up cannula 502. Hub 506 may further be provided with a conventional bleed back port 518 in which blood will become visible when the tip 504 of cannula 502 has entered blood vessel 16.

Once sheath 500 is properly positioned in the patient, with cannula tip 504 residing in blood vessel 16, the sheath is firmly held in place by a physician as transfer sleeve 400 is inserted into the proximal end of hub 506. Referring to FIG. 10B, as deployment instrument 200 is pushed toward hub 506, transfer sleeve 400 will slide distally through the hub until the enlarged rim 402 at the proximal end of the transfer sleeve is received in hub recess 514, and contacts annular wall 516 to prevent further advancement. The continued movement of deployment instrument 200 in the distal direction causes hemostasis device 30 connected to the distal end of ratchet pusher 304 to advance out from the distal end of transfer sleeve 400 and into cannula 502, as shown in FIG. 10C.

Figure 12A:
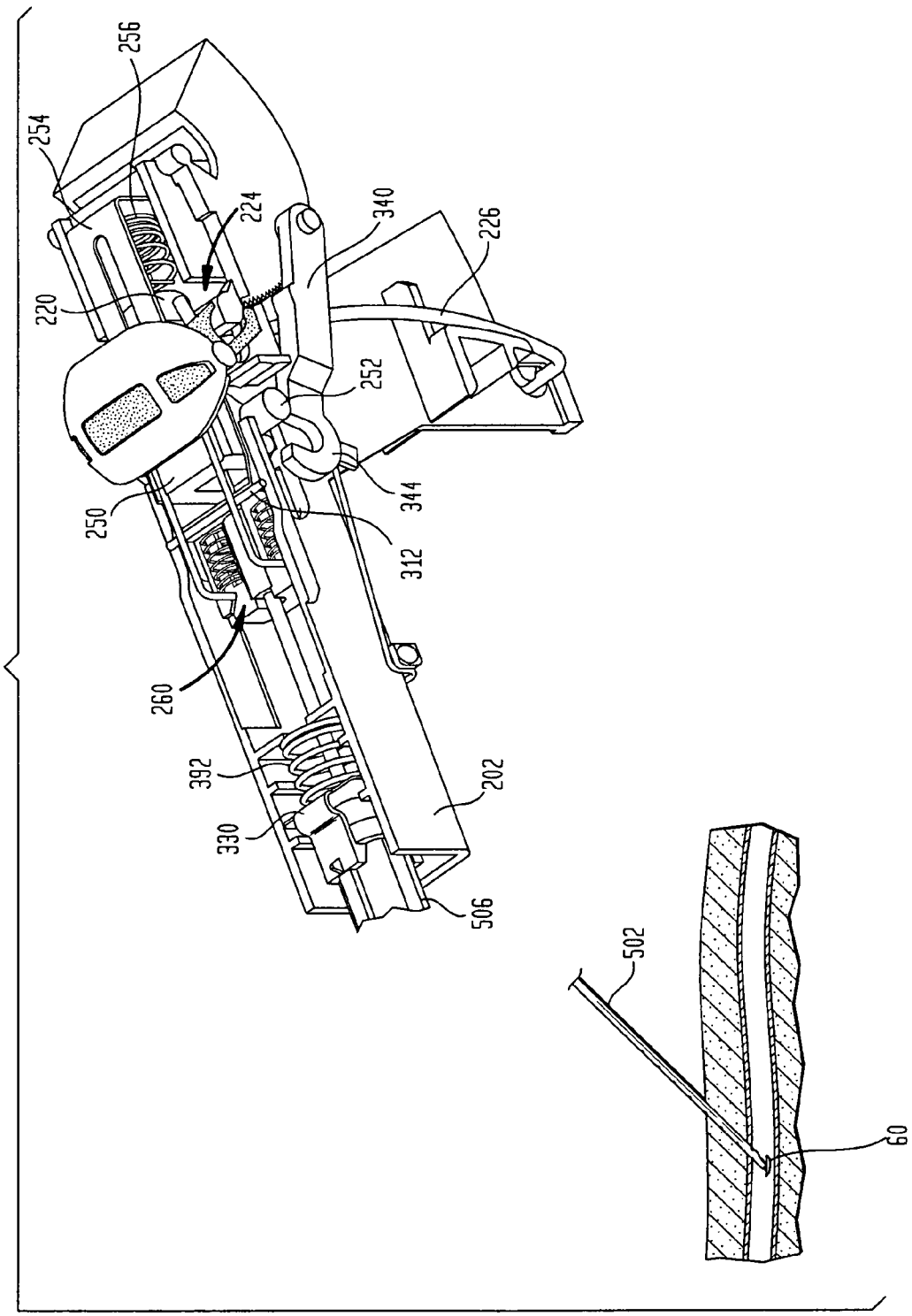

Hemostasis device 30 will continue to advance distally through cannula 502 until foot 60 thereof is expelled from the cannula through tip 504. Because of the relative lengths of cannula 502 and ratchet pusher 304, foot 60 of hemostasis device 30 will begin to protrude from the tip of the cannula as inclined surface 510 of connector 508 contacts catch members 390. Additional movement of deployment instrument 200 distally will further expel foot 60 of the hemostasis device from cannula 502 while connector 508 pushes catch 380 proximally in barrel 202 against the biasing force of spring 392. Ultimately, the distal movement of deployment instrument 200 will cause foot 60 of the hemostasis device to be fully expelled from cannula 502 and to move away from tip 504 thereof as spring 392 is compressed until the resilient force of catch fingers 388 is overcome and catch members 390 capture connector 508, as illustrated in FIG. 11. As this occurs, the biasing force of spring 392 will push cannula 502 distally until the tip 504 thereof abuts surface 62 of foot 60, pivoting foot 60 to an orientation substantially orthogonal to rigid post 40, as shown in FIG. 12A. The mating engagement of catch members 390 with connector 508 causes an audible click which alerts the physician that foot 60 of hemostasis device 30 has been fully deployed from cannula 502. Therefore, further advancement of deployment instrument 200 in the distal direction is not necessary.

With foot 60 fully deployed, deployment instrument 200 is pulled proximally, as shown in FIG. 12B, withdrawing cannula 502 from blood vessel 16 until the surface 62 of foot 60 contacts the inner surface of the blood vessel. Continued pulling of deployment instrument 200 in the proximal direction will place tension rod 232 under tension and cause tensioning hub 220 to begin to move distally relative to barrel 202 against the biasing force of tension spring 226. The distal movement of hub 220 will, in turn, push drive block 250 distally relative to barrel 202, and with it, puller/pusher carriage 260. As a result of the distal movement of drive block 250, the bosses 252 on either side thereof will begin to move toward the catches 344 on the free ends of deployment links 340. However, due to the presence of tab 314 of safety lockout 312 behind the spine 292 of upper carriage member 266, there is no relative movement between drive block 250 and puller/pusher carriage 260, and therefore no advancement of ratchet 100 on rigid post 40.

It will be appreciated from the foregoing description and the description which follows that the components of deployment instrument 200 are not moving in the distal direction relative to the patient, but rather barrel 202 and hand grip 204 are moving in the proximal direction as the other components remain in place. However, this can be seen as the movement of the components of deployment instrument 200 distally relative to barrel 202 and hand grip 204. Therefore, for convenience of explaining the operation of deployment instrument 200, the descriptions herein will be made in terms of the various components of deployment instrument 200 moving distally relative to barrel 202.

As deployment instrument 200 continues to be moved proximally, greater tension will be generated in tension rod 232, causing tensioning hub 220 (and drive block 250 and puller/pusher carriage 260) to continue to move distally relative to barrel 202 as arms 222 of hub 220 enter catches 370 of safety indicator 360. Up until this point, the pawls 230 on arms 222 (and, in fact, the arms themselves) have been positioned in the movement path of trigger 240, thus preventing trigger 240 from being actuated. However, as arms 222 move into catches 370, the pawls 230 thereof will begin to move away from the edges of trigger 240. At the same time, bosses 252 on drive block 250 will move closer to the catches 344 on deployment links 340.

Further movement of deployment instrument 200 proximally, and the resultant distal movement of arms 222 of tensioning hub 220 relative to barrel 202, will eventually cause safety indicator 360 to pivot in a clockwise direction (as shown in FIG. 12C) such that the "go/no go" indicia 366 and 368 appearing in window 364 begin to move from a "no go" condition indicated by indicia 366 to a "go" condition indicated by indicia 368. Bosses 252 on drive block 250 will move closer to catches 344 until they become positioned above the U-shaped openings of the catches. When this position is reached, the upward biasing force of tension spring 346 will push deployment links 340 upward until bosses 252 reside within catches 344. A further slight increase in tension in tension rod 232 will cause the "go/no go" indicia to move entirely to the "go" condition indicated by indicia 368 and pawls 230 to move to a position clear of the movement path of trigger 240, releasing the trigger for actuation. At this juncture, shown in FIG. 12D, arms 222 of tensioning hub 220 will be positioned adjacent the distal ends of cutouts 224 in sidewalls 208 and 210, such that hub 220 and tension rod 232 connected thereto will be prevented from moving any further distally relative to barrel 202. Moreover, as bosses 316 of safety lock-out 312 have not yet reached inclined surfaces 318 on sidewalls 208 and 210, safety lock-out 312 remains in its initial position, such that ratchet drive assembly 214 is not actuated and ratchet 100 is not advanced on rigid post 40.

As trigger 240 is actuated, pressure is applied to transverse member 324 to rotate the trigger in the clockwise direction (as shown in FIG. 12D). Rotation of trigger 240 causes deployment links 340 to move distally relative to barrel 202, pushing drive block 250 in the distal direction. This results in the simultaneous movement of puller/pusher carriage 260 in the distal direction through the connection with drive links 262, as well as a similar movement of safety lock-out 312. Since tensioning hub 220 is prevented from distal movement, tension rod 232 remains stationary while ratchet pusher 304 moves distally, with the result that ratchet 100 begins to move downward on rigid post 40.

The actuation of trigger 240 requires that a certain minimum amount of tension be maintained on tension rod 232. Any relaxation of this tension below the minimum will cause tension spring 226 to bias pawls 230 into engagement with the serrations 332 on the arms 322 of trigger 240, locking the trigger in place and preventing further advancement of ratchet 100 to its seated position.

Figure 12E:
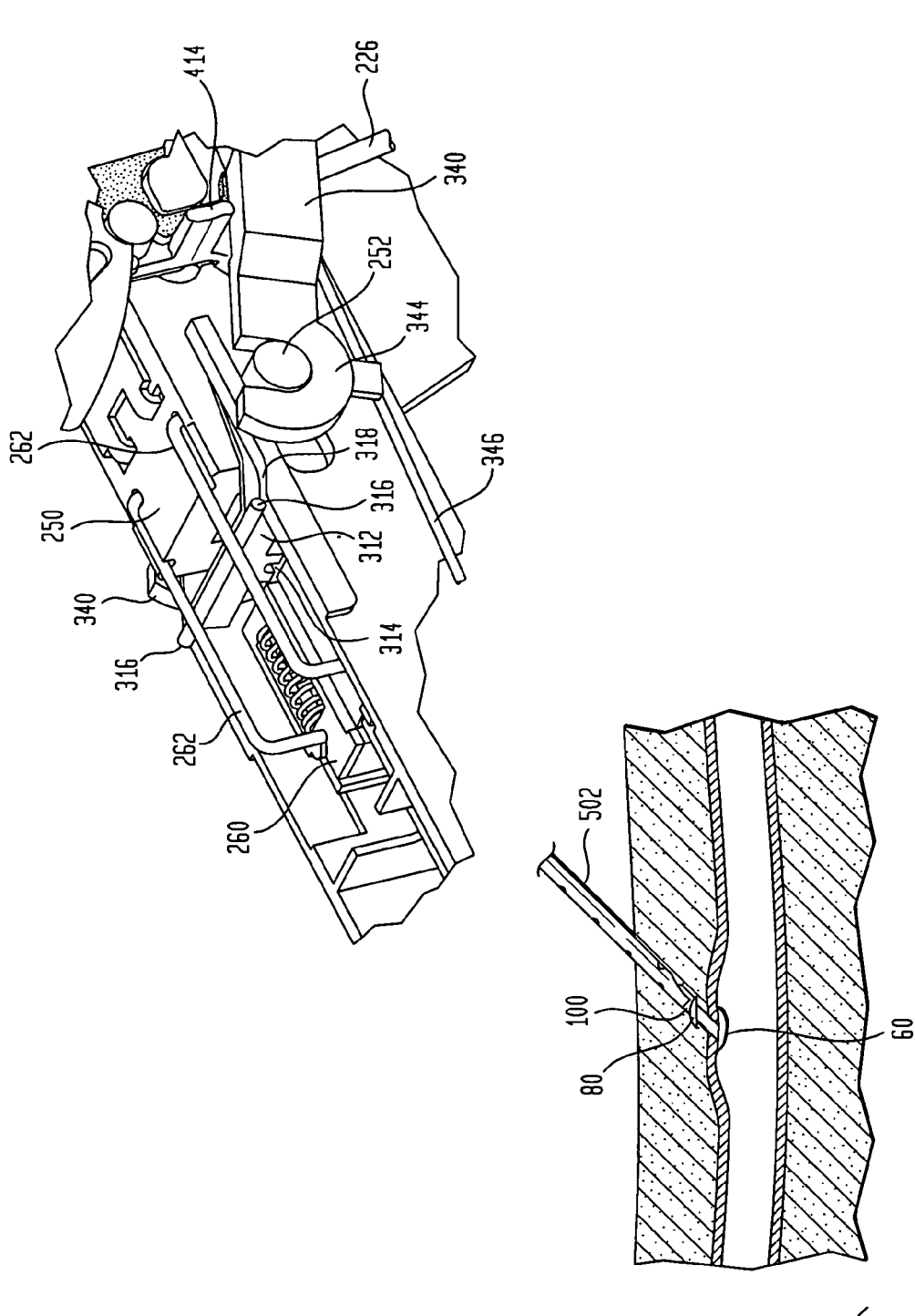

Further operation of trigger 240 will result in the further distal movement of drive block 250 relative to barrel 202, accompanied by puller/pusher carriage 260 and safety lockout 312, until the bosses 316 at either side of the safety lock-out are pushed up inclined surfaces 318, and tab 314 is clear of the puller/pusher carriage. The distal movement of puller/pusher carriage 260 will further drive ratchet pusher 304 distally, pushing ratchet 100 and seal 80 toward foot 60. At about the time safety lock-out 312 becomes disengaged from puller/pusher carriage 260, ratchet 100 will be expelled from the distal tip 504 of cannula 502, all of which is illustrated in FIG. 12E.

Referring to FIG. 12F, continued actuation of trigger 240 will cause ratchet pusher 304 to push ratchet 100 and seal 80 distally until the surface 82 of seal 80 contacts the outside wall of blood vessel 16, trapping the blood vessel wall between foot 60 and seal 80 so as to close the puncture wound 14 in the blood vessel. Further actuation of trigger 240 will increase the clamping pressure exerted by foot 60 and seal 80 on blood vessel 16 until one of two events occurs—either a predetermined maximum clamping pressure has been reached or ratchet pusher 304 has reached its maximum travel limit. If the maximum clamping pressure has been reached before ratchet pusher 304 has reached its maximum travel limit, continued actuation of trigger 240 will continue to advance drive block 250 distally relative to barrel 202, carrying with it drive links 262. Because they are captured within angled slots 288 and 290 of lower carriage member 264, the distal movement of drive links 262 will drive lower carriage member 264 distally while upper carriage member 266 remains stationary due to the inability of ratchet 100 to advance any further on post 40. Since safety lock-out 312 has been raised so that tab 314 thereof is above puller/pusher carriage 260, drive block 250 is able to move closer to the puller/pusher carriage, closing the space therebetween. The distal movement of drive links 262 and lower carriage member 264 relative to upper carriage member 266 will cause the drive links to advance along slots 300 in upper carriage member 266, compressing springs 310, until tabs 302 on the upper carriage member no longer traverse slots 288 and 290. At this point, drive links 262 will be freed to move distally out of slots 288 and 290, decoupling ratchet pusher 304 from the distal movement of drive block 250, and the biasing force exerted by springs 310 will retract lower carriage member 264 proximally until the front wall thereof contacts the front edges of wings 294 on upper carriage member 266. Drive links 262 will then be positioned distally of puller/pusher carriage 260.

Alternatively, if the maximum clamping pressure has not been reached, continued actuation of trigger 240 will advance drive block 250 distally relative to barrel 202, along with drive links 262 and the puller/pusher carriage 260 associated therewith. Again referring to FIG. 12F, puller/pusher carriage 260 will continue to advance distally in barrel 202 until the tips of tabs 302 on upper carriage member 266 contact abutment surfaces 410 formed on the inside surfaces of sidewalls 208 and 210. The engagement of tabs 302 with abutment surfaces 410 will prevent further movement of upper carriage member 266 as drive block 250 and lower carriage member 264 continue to advance distally until drive links 262 are freed from slots 288 and 290 as described above, and the ratchet pusher 304 is decoupled from the distal movement of drive block 250. The biasing force exerted by springs 310 will retract lower carriage member 264 proximally until the front wall 268 thereof contacts the front edges of wings 294 on upper carriage member 266, with drive links 262 positioned distally of puller/pusher carriage 260.

Once hemostasis device 30 has been deployed, further actuation of trigger 240 will continue to drive deployment links 340 distally until a cam surface 412 on each deployment link contacts a fixed lobe 414 extending outwardly from each of sidewalls 208 and 210. As shown in FIG. 12G, the engagement of cam surfaces 412 with lobes 414 will cause deployment links 340 to pivot downwardly against the biasing force of tension spring 346, releasing catches 344 from bosses 252 on drive block 250. Once bosses 252 are released, the biasing force of spring 256 will pull drive block 250 proximally toward hub 220, along with puller/pusher carriage 260, withdrawing ratchet pusher 304 relative to tension rod 232. Because puller/pusher carriage 260 is held adjacent drive block 250 by drive links 262, and is not spaced therefrom from by safety lock-out 312, puller/pusher carriage 260 will withdraw to a more proximal position than its starting position, thereby exposing end portion 238 of tension rod 232 and freeing the connection between the tension rod and rigid post 40 of the hemostasis device. Deployment instrument 200 may then be withdrawn and with it sheath 500, leaving hemostasis device 30 in place in the puncture wound, as illustrated in FIG. 12H.

Optionally, once hemostasis device 30 has been deployed, a mass of collagen or other hemostatic material may be placed in tissue channel 18 outside of blood vessel 16 to promote clotting of any blood that may leak out from the blood vessel. The hemostatic material may be in any form, including but not limited to, a liquid, gel, loose fibers, sponge, or compressed plug.

Where hemostasis device 30 includes a plate 110 of collagen or other hemostatic material, the procedure for deploying hemostasis device 30 will be substantially the same as that described above. However, rather than advancing seal 80 along rigid post 40 until surface 82 of seal 80 contacts the outer wall of blood vessel 16, seal 80 will be advanced downwardly until the plate 110 of hemostatic material contacts blood vessel 16, with both the blood vessel wall and plate 110 clamped between foot 60 and seal 80.

Figure 12H:
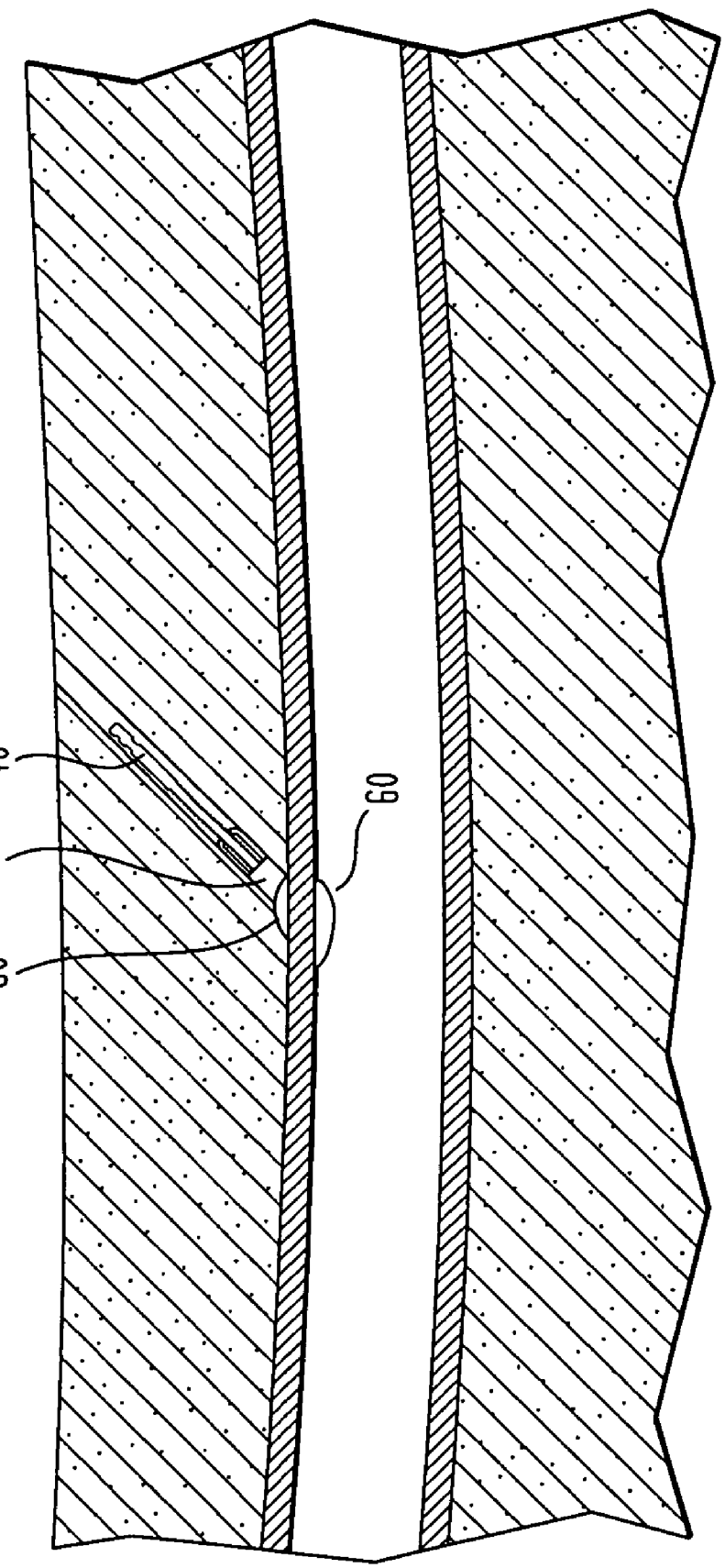

With hemostasis device 30 in its fully deployed position as shown in FIG. 12H, foot 60 thereof occupies only a very small portion of the cross-section of blood vessel 16, and thus does not impede the flow of blood therethrough. Since all of the components of hemostasis device 30 are formed of resorbable materials, the hemostasis device can be left in place within the body until it is fully absorbed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth herein can be combined in different ways than presented in the initial claims. It will also be appreciated that the features described in connection with individual embodiments may be shared with others of the described embodiments.

The invention claimed is:

1. A hemostasis device for percutaneously closing a puncture in the wall of a blood vessel, comprising:
    a rigid post having a length;
    first and second clamping members pivotally mounted on the rigid post, upon pivoting a first end of the first clamping member extends distally and a second end of the first clamping member extends proximally relative to a distal end of the rigid post;
    the first clamping member being sized for insertion through the puncture in the wall of the blood vessel and having a first face capable of engaging an inside surface of the blood vessel adjacent the puncture;
    the second clamping member being movable along the rigid post toward the first clamping member and having a first face capable of engaging an outside surface of the blood vessel adjacent the puncture; and
    the first and second clamping members being spaced relatively far apart along the length of the rigid post in an initial collapsed state wherein the first and second clamping members are each in a first pivoted position, and being relatively close together in a deployed state wherein the first and second clamping members are each in a second pivoted position capable of sandwiching the wall of the blood vessel.

2. The hemostasis device as claimed in claim 1, further comprising:
    a retaining member for retaining the second clamping member adjacent the outside surface of the blood vessel in the deployed state.

3. The hemostasis device as claimed in claim 2, wherein the length of the rigid post includes a plurality of teeth, and the retaining member includes at least one pawl for engaging the plurality of teeth, whereby the engagement of the at least one pawl with the plurality of teeth resists movement of the retaining member relative to the rigid post.

4. The hemostasis device as claimed in claim 3, wherein the rigid post includes at least one recess at a proximal end thereof, the recess being sized to receive the at least one pawl of the retaining member for holding the retaining member in a fixed position relative to the rigid post in the initial collapsed state.

5. The hemostasis device as claimed in claim 1, wherein the rigid post includes a first portion and a second portion connected in end-to-end relationship so as to define an oblique angle between the first portion and the second portion.

6. The hemostasis device as claimed in claim 5, wherein the oblique angle is between about 120° and about 150°.

7. The hemostasis device as claimed in claim 6, wherein the oblique angle is about 135°.

8. The hemostasis device as claimed in claim 5, wherein the first portion of the rigid post includes a plurality of teeth formed along a length thereof, and the second portion of the rigid post is devoid of teeth.

9. The hemostasis device as claimed in claim 5, wherein the first clamping member includes an aperture formed at an acute angle to the first face of the first clamping member, the aperture being sized to receive the second portion of the rigid post.

10. The hemostasis device as claimed in claim 9, wherein the acute angle is between about 30° and about 60°.

11. The hemostasis device as claimed in claim 10, wherein the acute angle is about 45°.

12. The hemostasis device as claimed in claim 11, wherein the acute angle is complementary to the oblique angle between the first portion and the second portion of the rigid post.

13. The hemostasis device as claimed in claim 1, wherein the rigid post includes a substantially linear first portion and a substantially linear second portion, the first portion being axially offset from the second portion in two orthogonal directions to define a shallow recess in the rigid post.

14. The hemostasis device as claimed in claimed 13, wherein the shallow recess is sized to accommodate one end of the second clamping member in the initial collapsed state.

15. The hemostasis device as claimed in claim 1, wherein the first clamping member has a width and a length greater than the width.

16. The hemostasis device as claimed in claim 15, wherein the first clamping member has a second surface which is smoothly curved in the length direction and the width direction.

17. The hemostasis device as claimed in claim 16, wherein the rigid post has an enlarged head at a distal end thereof, the enlarged head being recessed below the second surface of the first clamping member in the deployed state.

18. The hemostasis device as claimed in claim 1, wherein the rigid post and the first and second clamping members are formed from a resorbable material.

19. The hemostasis device as claimed in claim 18, wherein the resorbable material is a polymer.

20. The hemostasis device as claimed in claim 19, wherein the polymer includes copolymers of lactide and glycolide.

21. The hemostasis device as claimed in claim 1, wherein each of the first and second clamping members has an elongated shape and the first clamping member lies substantially parallel to the second clamping member in the deployed state.

22. The hemostasis device as claimed in claim 1, further comprising a plate of hemostatic material positioned on the rigid post between the first and second clamping members.

23. The hemostasis device as claimed in claim 22, wherein the plate of hemostatic material is connected to the first face of the second clamping member.

24. The hemostasis device as claimed in claim 23, wherein the plate of hemostatic material is adhered to the first face of the second clamping member by a biologically compatible adhesive.

25. The hemostasis device as claimed in claim 22, wherein the hemostatic material includes collagen.

26. A hemostasis device for percutaneously closing a puncture in the wall of a blood vessel, comprising:
   a rigid post;
   a first clamping member pivotally mounted on the rigid post and being sized for insertion through the puncture in the wall of the blood vessel, the first clamping member having a first face configured to engage an inside surface of the blood vessel adjacent to the puncture, upon pivoting a first end of the first clamping member extends distally and a second end of the first clamping member extends proximally relative to a distal end of the rigid post;
   a second clamping member pivotally mounted on the rigid post and being movable along the rigid post toward the first clamping member, the second clamping member having a first face configured to engage an outside surface of the blood vessel adjacent to the puncture, the second clamping members being movable from an initial collapsed state in a first pivoted position, to a deployed state in a second pivoted position, the entire second clamping member being pivotal relative to the rigid post, wherein the first and second clamping members when the second clamping member is in the deployed state are capable of sandwiching the wall of the blood vessel.

27. The hemostasis device as claimed in claim 26, wherein the first clamping device is movable from a first rotated position in an initial collapsed state, to a second rotated position in a deployed state.

28. The hemostasis device as claimed in claim 26, wherein the rigid post extends through the first clamping member.

29. The hemostasis device as claimed in claim 28, wherein the rigid post includes a head portion positioned at a distal end thereof that retains the first clamping member on the rigid post.

30. The hemostasis device as claimed in claim 29, wherein the first clamping member includes a second surface arranged opposite the first surface, wherein the head portion is recessed below the second surface of the first clamping member when the first clamping member is in a deployed state.

31. The hemostasis device as claimed in claim 26, further comprising a retaining member configured to retain the second clamping member adjacent to the outside surface of the blood vessel in the deployed state.

32. The hemostasis device as claimed in claim 31, wherein the rigid post includes a plurality of teeth, and the retaining member includes at least one pawl configured to engage the plurality of teeth to resist movement of the retaining member relative to the rigid post.

33. The hemostasis device as claimed in claim 26, wherein the rigid post includes a first portion and a second portion connected in end-to-end relationship so as to define an oblique angle between the first portion and the second portion.

34. The hemostasis device as claimed in claim 33, wherein the first clamping member includes an aperture formed at an acute angle to the first face of the first clamping member, the aperture being sized to receive the second portion of the rigid post.

35. A hemostasis device for percutaneously closing a puncture in the wall of a blood vessel, comprising:
   a rigid post;
   a first clamping member being sized for insertion through the puncture in the wall of the blood vessel and having a first face configured to engage an inside surface of the blood vessel adjacent to the puncture, the rigid post extending through the first clamping member, upon pivoting a first end of the first clamping member extends distally and a second end of the first clamping member extends proximally relative to a distal end of the rigid post;
   a second clamping member being movable along the rigid post toward the first clamping member and having a first face configured to engage an outside surface of the blood vessel adjacent to the puncture, the rigid post extending through the second clamping member, the entire second clamping member being pivotal relative to the rigid post;
   wherein the first and second clamping members being operable from an initial collapsed state relative to the rigid post, wherein the first and second clamping members when in the deployed state are capable of sandwiching the wall of the blood vessel.

36. The hemostasis device as claimed in claim 35, wherein the first clamping device is movable from a first rotated position in the collapsed state, to a second rotated position in the deployed state.

37. The hemostasis device as claimed in claim 35, wherein the rigid post includes a head portion positioned at a distal end thereof that retains the first clamping member on the rigid post.

38. The hemostasis device as claimed in claim 37, wherein the first clamping member includes a second surface arranged opposite the first surface, wherein the head portion is recessed below the second surface of the first clamping member when the first clamping member is in a deployed state.

39. The hemostasis device as claimed in claim 35, further comprising a retaining member configured to retain the second clamping member adjacent to the outside surface of the blood vessel in the deployed state.

40. The hemostasis device as claimed in claim 39, wherein the rigid post includes a plurality of teeth, and the retaining member includes at least one pawl configured to engage the plurality of teeth to resist movement of the retaining member relative to the rigid post.

41. The hemostasis device as claimed in claim 35, wherein the rigid post includes a first portion and a second portion connected in end-to-end relationship so as to define an oblique angle between the first portion and the second portion.

42. The hemostasis device as claimed in claim 41, wherein the first clamping member includes an aperture formed at an acute angle to the first face of the first clamping member, the aperture being sized to receive the second portion of the rigid post.

43. A hemostasis device for percutaneously closing a puncture in the wall of a blood vessel, comprising:
  a rigid post having a length and including a first portion and a second portion connected in end-to-end relationship so as to define an oblique angle between the first portion and the second portion;
  first and second clamping members pivotally mounted on the rigid post;
  the first clamping member being sized for insertion through the puncture in the wall of the blood vessel and having a first face capable of engaging an inside surface of the blood vessel adjacent the puncture;
  the second clamping member being movable along the rigid post toward the first clamping member and having a first face capable of engaging an outside surface of the blood vessel adjacent the puncture; and
  the first and second clamping members being spaced relatively far apart along the length of the rigid post in an initial collapsed state wherein the first and second clamping members are each in a first pivoted position, and being relatively close together in a deployed state wherein the first and second clamping members are each in a second pivoted position, wherein the first and second clamping members when in the deployed state are capable of sandwiching the wall of the blood vessel;
  wherein the first clamping member includes an aperture formed at an acute angle to the first face of the first clamping member, the aperture being sized to receive the second portion of the rigid post.

44. The hemostasis device as claimed in claim 43, wherein the acute angle is between about 30° and about 60°.

45. The hemostasis device as claimed in claim 44, wherein the acute angle is about 45°.

46. The hemostasis device as claimed in claim 43, wherein the acute angle is complementary to the oblique angle between the first portion and the second portion of the rigid post.

47. A hemostasis device for percutaneously closing a puncture in the wall of a blood vessel, comprising:
  a rigid post including a first portion and a second portion connected in end-to-end relationship so as to define an oblique angle between the first portion and the second portion;
  a first clamping member mounted on the rigid post and being sized for insertion through the puncture in the wall of the blood vessel, the first clamping member having a first face configured to engage an inside surface of the blood vessel adjacent to the puncture;
  a second clamping member pivotally mounted on the rigid post and being movable along the rigid post toward the first clamping member, the second clamping member having a first face configured to engage an outside surface of the blood vessel adjacent to the puncture, the second clamping members being movable from an initial collapsed state in a first pivoted position, to a deployed state in a second pivoted position, wherein the first and second clamping members when the second clamping member is in the deployed state are capable of sandwiching the wall of the blood vessel;
  wherein the first clamping member includes an aperture formed at an acute angle to the first face of the first clamping member, the aperture being sized to receive the second portion of the rigid post.

48. A hemostasis device for percutaneously closing a puncture in the wall of a blood vessel, comprising:
  a rigid post including a first portion and a second portion connected in end-to-end relationship so as to define an oblique angle between the first portion and the second portion;
  a first clamping member being sized for insertion through the puncture in the wall of the blood vessel and having a first face configured to engage an inside surface of the blood vessel adjacent to the puncture, the rigid post extending through the first clamping member;
  a second clamping member being movable along the rigid post toward the first clamping member and having a first face configured to engage an outside surface of the blood vessel adjacent to the puncture, the rigid post extending through the second clamping member;
  wherein the first and second clamping members being operable from an initial collapsed state relative to the rigid post, wherein the first and second clamping members when in the deployed state are capable of sandwiching the wall of the blood vessel;
  wherein the first clamping member includes an aperture formed at an acute angle to the first face of the first clamping member, the aperture being sized to receive the second portion of the rigid post.

* * * * *